United States Patent
Tu et al.

(10) Patent No.: US 10,653,722 B2
(45) Date of Patent: May 19, 2020

(54) HUMAN CD8+ REGULATORY T CELLS INHIBIT GVHD AND PRESERVE GENERAL IMMUNITY

(71) Applicant: THE UNIVERSITY OF HONG KONG, Hong Kong (HK)

(72) Inventors: Wenwei Tu, Hong Kong (HK); Yinping Liu, Hong Kong (HK); Jian Zheng, Hong Kong (HK)

(73) Assignee: THE UNIVERSITY OF HONG KONG, Hong Kong (HK)

( * ) Notice: Subject to any disclaimer, the term of this patent is extended or adjusted under 35 U.S.C. 154(b) by 0 days.

(21) Appl. No.: 16/004,491

(22) Filed: Jun. 11, 2018

(65) Prior Publication Data

US 2018/0289743 A1    Oct. 11, 2018

Related U.S. Application Data

(62) Division of application No. 14/596,368, filed on Jan. 14, 2015, now Pat. No. 10,092,597.

(60) Provisional application No. 61/927,046, filed on Jan. 14, 2014.

(51) Int. Cl.
| | |
|---|---|
| *A61K 35/17* | (2015.01) |
| *C12N 5/00* | (2006.01) |
| *C12N 5/0783* | (2010.01) |
| *A61K 35/12* | (2015.01) |

(52) U.S. Cl.
CPC ............ *A61K 35/17* (2013.01); *C12N 5/0637* (2013.01); *A61K 2035/122* (2013.01); *C12N 2502/1107* (2013.01)

(58) Field of Classification Search
CPC .................................................. C12N 5/0669
See application file for complete search history.

(56) References Cited

U.S. PATENT DOCUMENTS

| | | | |
|---|---|---|---|
| 6,447,765 B1 | 9/2002 | Horwitz | |
| 8,658,159 B2 * | 2/2014 | Tu .......................... | A61K 35/17 424/93.71 |
| 9,480,715 B2 * | 11/2016 | Tu .......................... | A61K 35/17 |
| 2003/0064067 A1 | 4/2003 | Masuyama | |
| 2006/0115899 A1 | 6/2006 | Buckner et al. | |
| 2007/0190052 A1 | 8/2007 | Herold et al. | |
| 2008/0063652 A1 | 3/2008 | Pykett et al. | |
| 2008/0279826 A1 | 12/2008 | Battaglia et al. | |
| 2009/0142308 A1 | 6/2009 | Orban et al. | |
| 2009/0297539 A1 | 12/2009 | Koshiba et al. | |
| 2009/0304659 A1 | 12/2009 | Banchereau et al. | |
| 2009/0324557 A1 | 12/2009 | Tu et al. | |
| 2010/0034786 A1 | 2/2010 | Merkenschlager | |
| 2010/0291678 A1 | 11/2010 | Blazar et al. | |
| 2010/0310588 A1 | 12/2010 | Bluestone et al. | |
| 2011/0052529 A1 | 3/2011 | Shirwan | |
| 2011/0123502 A1 | 5/2011 | Barry et al. | |
| 2011/0136208 A1 | 6/2011 | Breun et al. | |
| 2011/0287048 A1 | 11/2011 | Round et al. | |
| 2012/0207727 A1 | 8/2012 | Blazar et al. | |
| 2013/0164312 A1 | 6/2013 | Aarvak et al. | |

FOREIGN PATENT DOCUMENTS

| | | |
|---|---|---|
| EP | 2025747 | 2/2009 |
| EP | 2126054 | 12/2009 |
| JP | 2009-215284 | 9/2009 |
| RU | 2008104682 | 2/2010 |
| WO | 2006127152 | 11/2006 |
| WO | 2009155477 | 12/2009 |
| WO | 2010017220 | 2/2010 |
| WO | 2010129770 | 11/2010 |
| WO | 2012096376 | 7/2012 |

OTHER PUBLICATIONS

Non-Final Office Action dated Jul. 27, 2016 corresponding to U.S. Appl. No. 14/596,368 filed Jan. 14, 2015.
Final Office Action dated Jan. 12, 2017 corresponding to U.S. Appl. No. 14/596,368 filed Jan. 14, 2015.
Final Office Action dated Dec. 14, 2017 corresponding to U.S. Appl. No. 14/596,368 filed Jan. 14, 2015.
Final Office Action dated Jul. 3, 2017 corresponding to U.S. Appl. No. 14/596,368 filed Jan. 14, 2015.

* cited by examiner

*Primary Examiner* — Ruth A Davis
(74) *Attorney, Agent, or Firm* — Amin, Turocy & Watson, LLP

(57) ABSTRACT

Graft-versus-host disease (GVHD) is a lethal complication of allograft transplantation. The current strategy of using immunosuppressive agents to control GVHD may cause general immune suppression and limit the effectiveness of allograft transplantation. Adoptive transfer of regulatory T cells (Treg) can prevent GVHD in rodents, indicating the therapeutic potential of Treg for GVHD in humans. However, the clinical application of Treg-based therapy is hampered by the low frequency of human Treg and the lack of a reliable model to test their therapeutic effects in vivo. Human alloantigen-specific Treg are generated from antigenically-naïve precursors in a large scale ex vivo using allogeneic activated B cells as stimulators. Here, a human allogeneic GVHD model is established in humanized mice to mimic GVHD after allograft transplantation in humans. The ex vivo-induced $CD8^{hi}$ Treg can control GVHD in an allo-specific manner by reduction of alloreactive T-cell proliferation, and inflammatory cytokine and chemokine secretion within target organs through a CTLA-4-dependent mechanism in humanized mice. Importantly, the Tregs can induce long-term tolerance effectively without compromising general immunity and graft-versus-tumor (GVT) activity.

3 Claims, 9 Drawing Sheets

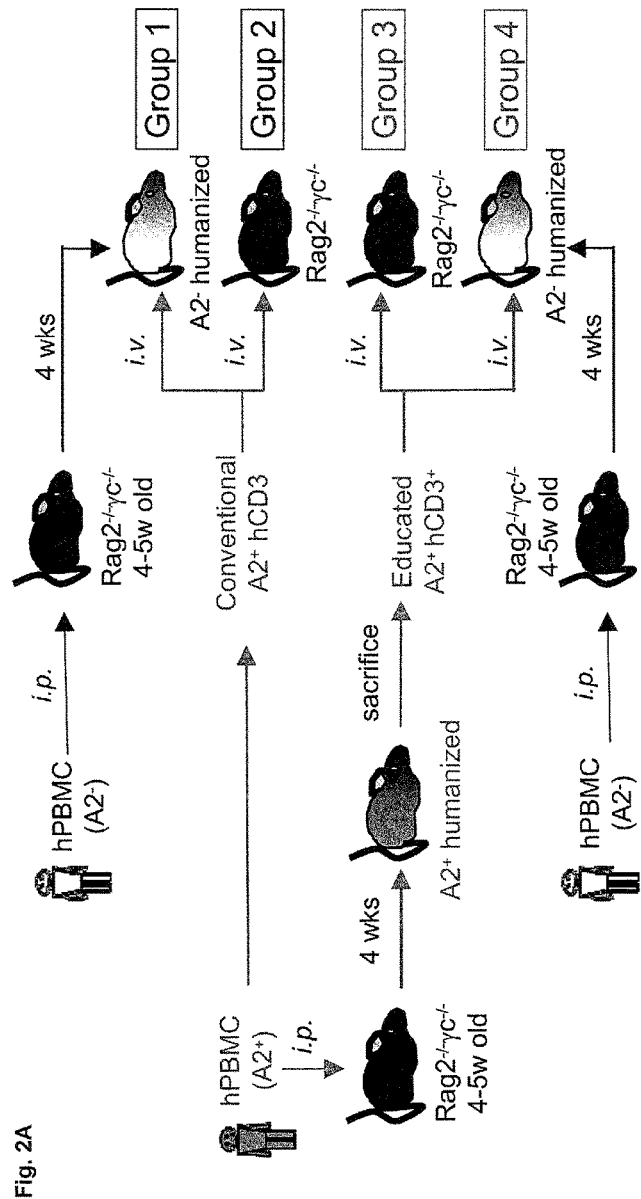
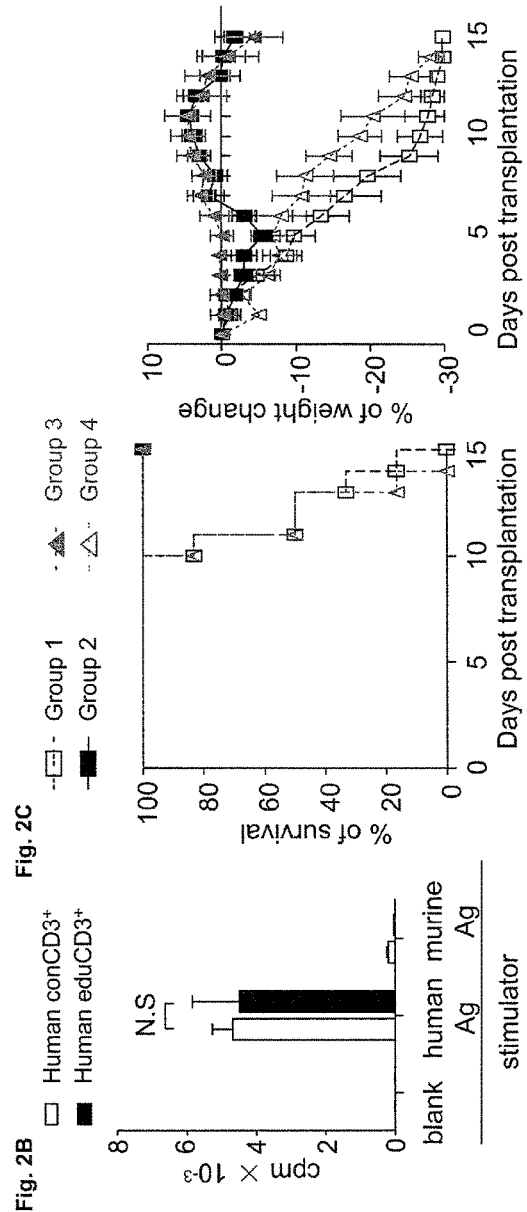
Fig. 2A
Fig. 2B
Fig. 2C

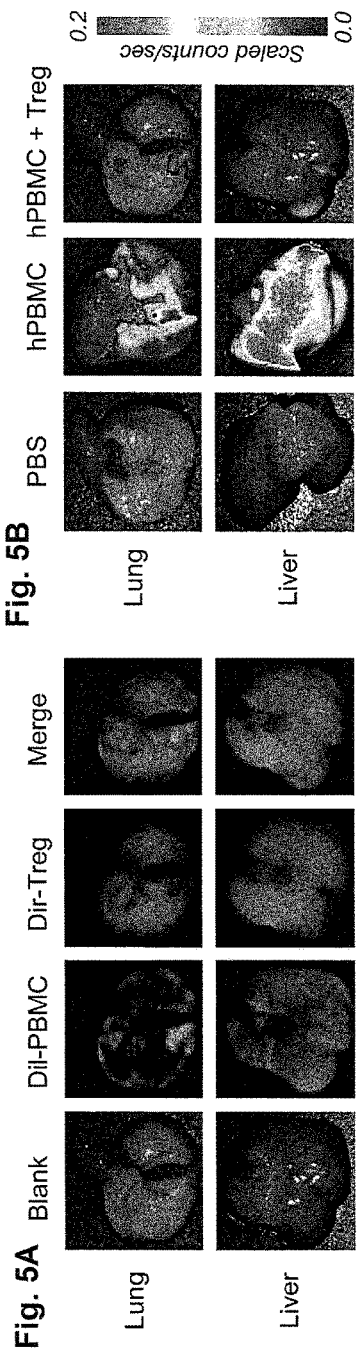
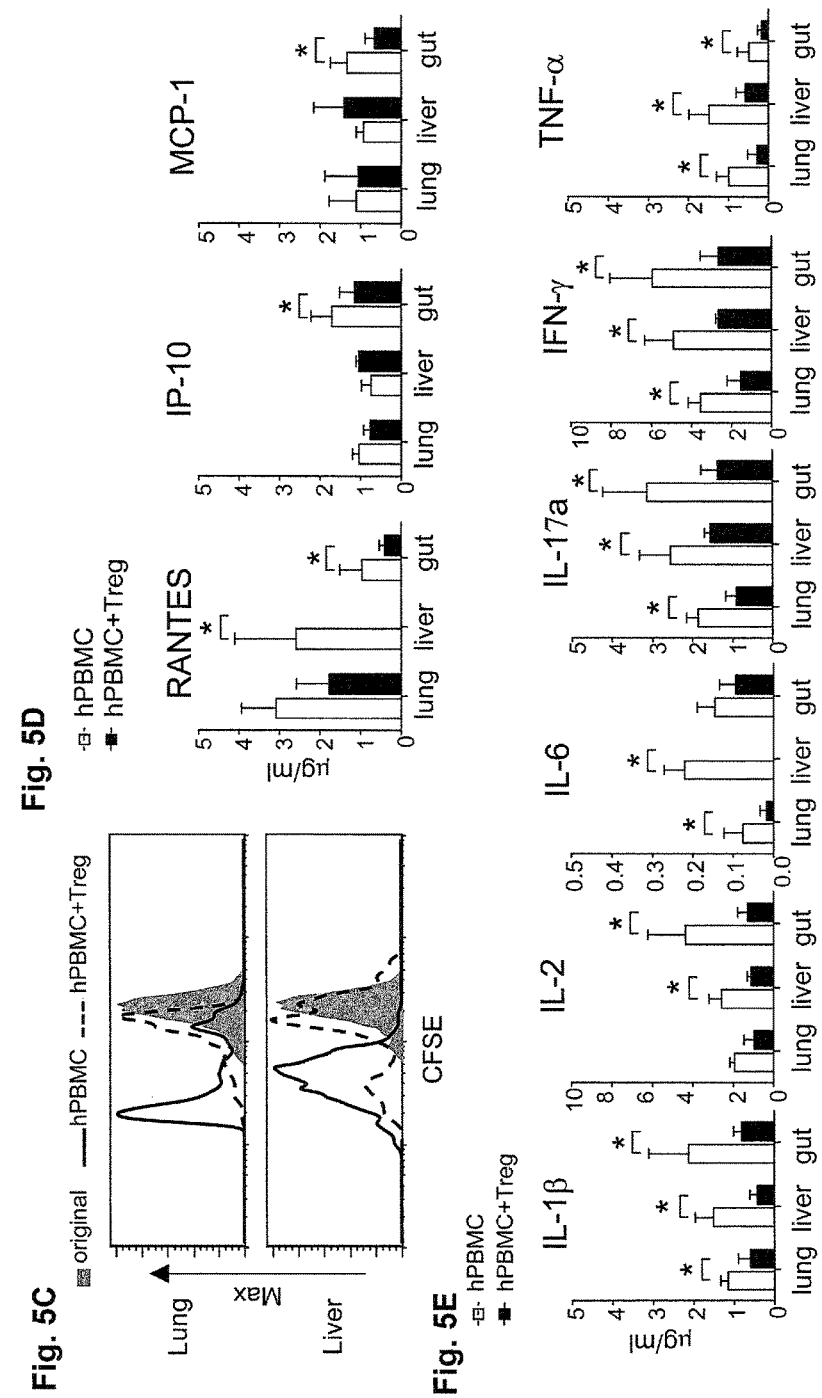

HUMAN CD8+ REGULATORY T CELLS INHIBIT GVHD AND PRESERVE GENERAL IMMUNITY

CROSS REFERENCE TO RELATED APPLICATIONS

This application is a Divisional of application Ser. No. 14/596,368 filed on Jan. 14, 2015, the entire contents of which are incorporated herein by reference.

This application claims priority to Provisional application Ser. No. 61/927,046, filed on Jan. 14, 2014, which is incorporated herein by reference.

TECHNICAL FIELD

The subject matter described herein relates to various aspects associated with inhibiting graft-versus-host disease while preserving general immunity of the host/recipient and graft versus tumor effects.

BACKGROUND

Bone marrow transplantation (BMT) is now widely accepted as an effective treatment for malignant and non-malignant hematologic diseases. However, graft-versus-host disease (GVHD) is a lethal complication of allogeneic BMT. GVHD is a condition that can occur after an allogeneic transplant. In GVHD, the immune cells in the donated bone marrow attacks the recipient's tissue and organs as foreign invaders. Treating GVHD relies on the general suppression of the immune system, but this treatment leads to severe side effects like tumor reoccurrence or opportunistic infection.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Rather, the sole purpose of this summary is to present some concepts of the invention in a simplified form as a prelude to the more detailed description that is presented hereinafter.

One embodiment involves a method for inhibiting GVHD in a patient-recipient due to bone marrow transplantation, comprising obtaining a sample of naïve T cells from the donor of bone marrow; co-culturing B cells from the patient-recipient of bone marrow with naïve T cells from the donor in a suitable ratio in the absence of exogenous cytokines for a period of time sufficient to generate alloantigen-specific human regulatory T cells; and administering the alloantigen-specific human regulatory T cells to the patient-recipient of bone marrow.

Another embodiment involves a method for inhibiting a patient-recipient from allogeneic rejection against tissue, cell, graft, or organ transplant mediated by immune cells from a donor, comprising obtaining a sample of naïve T cells from the patient-recipient; co-culturing allogeneic B cells from the donor of tissue, cell, graft, or organ with naïve T cells from the patient-recipient in a suitable ratio in the absence of exogenous cytokines for a period of time sufficient to generate alloantigen-specific human regulatory T cells; and administering the alloantigen-specific human regulatory T cells to the patient-recipient of tissue, cell, graft, or organ transplant.

Yet another embodiment involves a method for preventing allergic asthma or airway hypersensitivity in a patient, comprising obtaining a sample of naïve T cells from the patient; co-culturing allergen-loaded B cells from the patient with their own naïve T cells in a suitable ratio for a period of time sufficient to generate allergen-specific human regulatory T cells; and administering allergen-specific autologous human regulatory T cells to the patient.

To the accomplishment of the foregoing and related ends, the invention comprises the features hereinafter fully described and particularly pointed out in the claims. The following description and the annexed drawings set forth in detail certain illustrative aspects and implementations of the invention. These are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF DRAWINGS

FIGS. 2A-2C depict a graphical illustration of recipient-specific donor $CD8^{hi}$ Treg suppressing the acute proliferation of donor T cells in target organs after donor hPBMC transplantation.

FIGS. 5A-5E illustrate chimerism in humanized recipient mice ($A2^-$) before and after transplantation of allogeneic hPBMC ($A2^+$) and $CD8^{hi}$ Treg ($A2^+$).

DETAILED DESCRIPTION

Figure 1A:
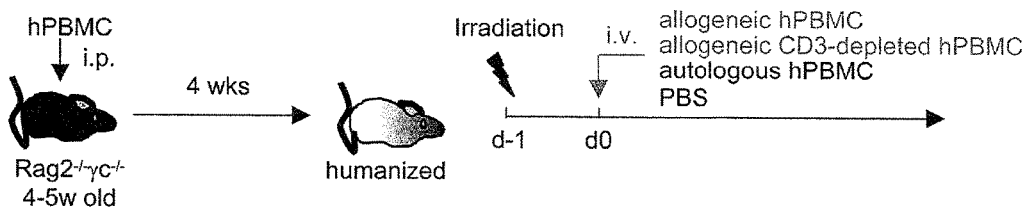
FIGS. 1A-1E depict a GVHD model including illustrating the effects of $CD8^{hi}$ Treg on inflammatory cytokine production by $CD4^+$ and $CD8^+$ T cells from donor PBMC in vitro.

The current strategy of controlling GVHD by depletion (1) or general inhibition (2) of donor T cells using immunosuppressive agents may cause general immune suppression, resulting in tumor relapse or opportunistic infection, and limiting the effectiveness of BMT (2). The ideal for BMT would be to induce a sustained state of specific tolerance to alloantigen with minimal or no conventional immunosuppressive drugs.

Alloantigen-specific regulatory T cells (Treg), as the negative regulators of immune responses to alloantigen, are critical for maintaining alloantigen-specific tolerance (3-5). In addition to the well-described role of $CD4^+$ Treg in suppressing excessive immune responses (6, 7), $CD8^+$ Treg has also been reported to play important roles in maintaining immune tolerance (8-12). Adoptive transfer of murine alloantigen-specific Treg can prevent GVHD and allograft rejection in mouse models (5, 13), indicating that Treg-based therapy has a great therapeutic potential for these diseases in humans. However, the clinic application of Treg-based therapy is limited by the low frequency of human Treg and the lack of a reliable model to evaluate their therapeutic effects in vivo.

Although several protocols have been developed for generation of human CD8+ Treg (14-19), none has been robust in terms of being of a practical scale for clinical use. Recently, using allogeneic CD40-activated B cells as the tolerogenic antigen presenting cells (20-22) to stimulate naïve CD8+CD25− T cells, we developed a simple, cost-effective novel protocol to rapidly induce and expand large numbers of functional human alloantigen-specific CD8+ Treg. The induced CD8+ Treg expressed higher levels of CD8 on their surface than their precursors and are thus identified as $CD8^{hi}$ Treg (23).

In vivo studies of human CD4+ Treg in immunodeficient mice showed that human CD4+ Treg can prevent the rejection of human skin allograft and the development of transplant atherosclerosis (24, 25). However, as the immunodeficient mice used in these studies did not contain a stable human immune system before the adoptive transfer of human Treg, the relevance of these results to human disease is unclear. In addition, the in vivo function of ex vivo-induced human CD8+ Treg still remains unknown. Therefore, developing more reliable models to mimic human diseases and evaluate the function of the ex vivo-induced human Treg is urgently required.

Previously, we successfully established a complete human immune system in C57BL/10SgAiRag2−/−γc−/− (Rag2−/−γc−/−) mice reconstituted with human peripheral blood mononuclear cells (hPBMC) (26). In this study, we further established a novel human allogeneic acute GVHD model on these "humanized mice" and investigated the therapeutic potential of $CD8^{hi}$ Treg in preventing GVHD in vivo. We demonstrate here that human $CD8^{hi}$ Treg induced ex vivo by allogeneic CD40-activated B cells can ameliorate acute GVHD in an allo-specific manner via reduction of alloreactive T cell proliferation and inflammatory cytokines secretion within target organs through a CTLA-4 dependent mechanism. Importantly, these $CD8^{hi}$ Treg can induce long-term tolerance effectively without compromising general immunity and GVT activity in humanized mice. Our results support testing of ex vivo-induced human $CD8^{hi}$ Treg in preventing and treating GVHD in clinical trials.

Here we developed a high-efficient and low-cost ex vivo system by using allogeneic CD40-activated B cells to induce and expand human antigen-specific $CD8^{hi}$ regulatory T cells (Tregs) at a large scale. Investigation on a novel GVHD model established in "humanized mice" suggested that these $CD8^{hi}$ Tregs could potently inhibit GVHD in an antigen-specific manner while preserving general immunity of host and graft versus tumor (GVT) effects. The ex vivo system using allogeneic CD40-activated B cells to induce and expand human antigen-specific $CD8^{hi}$ Tregs is a new strategy to generate clinical-scale antigen-specific Tregs for treating immune-related diseases.

For example, by using this highly-efficient and low-cost system to induce and expand antigen-specific $CD8^{hi}$ Tregs, only 10 ml donor and 5 ml recipient will be required to generate clinic-grade Tregs, which significantly improve the potential of its clinical application. Secondly, our results suggested that one dose of $CD8^{hi}$ Tregs is enough for inducing long-term antigen-specific tolerance while preserving general functions of reinstituted immune system in recipients, which can minimize the usage of immunosuppressive drugs and greatly improve the life quality of patients accepting bone marrow transplantation. Finally, as the ex vivo-induced $CD8^{hi}$ Tregs are recipient-specific, it is unnecessary to find a donor with good human leukocyte antigens (HLA) match for a patient (recipient) eventually, which can significantly resolve the major problem for BMT-difficult to find a good HLA match donor for a patient. In other words, it is no longer necessary to consider HLA-match for BMT as this Treg-based therapy can be successfully translated into clinical systems.

One of the major obstacles for Treg-based therapy is the lack of reliable models to test the therapeutic effects of human Treg in vivo. More recently, the in vivo function of the ex vivo-induced human CD4+ Treg has been evaluated in immunodeficient mice (24, 25). However, the relevance of the results to human disease remains unclear because the immunodeficient mice do not contain a stable human immune system before the adoptive transfer of human Treg. Here, by adoptive transfer of allogeneic hPBMC into humanized mice with a stable reconstitution of human immune system (26), we successfully establish a novel human allogeneic acute GVHD model in humanized mice. Similar to humans (28, 29), the acute GVHD is mediated mainly by donor CD3+ T cells and characterized by disease appearance (hunching, activity, ruffling and diarrhea), recruitment of alloreactive cells in target organs, and dys-regulation of pro-inflammatory chemokines and cytokines. Importantly, using mouse-educated human CD3+ T cells, we further demonstrated that the acute GVHD is mediated mainly by human allogeneic responses but not by xenogeneic response. The human allogeneic GVHD model established here may provide a more relevant approach for studies of human immunopathogenesis and therapeutics for GVHD after BMT.

Different from other antigen-specific CD8+ Treg which are difficult to be expanded (14-19), human $CD8^{hi}$ Treg induced ex vivo by allogeneic hCD40-B cells have highly secondary proliferative capacity thereby they are easy to be expanded in large scale (23).

Importantly, it is unnecessary to add any exogenous cytokines for inducing and expanding $CD8^{hi}$ Treg, because hCD40-B cells can secrete substantial amounts of IL-2 (20). This lack of requirement for exogenous cytokines could significantly reduce the cost for the generation of human $CD8^{hi}$ Treg. In addition, the $CD8^{hi}$ Treg not only express high level of Foxp3 and CTLA-4 but also have higher level of CD8 and CD25 expression on their surface compared to their precursors, thus making it easy to purify them from co-culture.

The importance of CD8+ Treg in the induction of tolerance during transplantation has been confirmed in rodents recently. It has been shown that murine CD8+Foxp3+ Treg were induced during GVHD after allogeneic BMT, and the induction of these Treg was correlated positively with the protection of GVHD in mice (30, 31). In a heart transplant model, the accumulation of rat CD8+ Treg in allograft was found to be associated with tolerance induction in allograft recipients (32). By adoptive transfer, the ex vivo-induced CD8+Foxp3+ Treg prevented the skin allograft rejection in mice (13). Here, using human $CD8^{hi}$ Treg induced by allogeneic hCD40-B cells ex vivo, we found that they can suppress the proliferation and inflammatory cytokine and chemokine secretion in alloreactive T cells in vitro. In the human allogeneic acute GVHD model, we further demonstrated that these ex vivo induced human $CD8^{hi}$ Treg can effectively control acute GVHD in an allo-specific manner by reduction of alloreactive T-cell proliferation and inflammatory cytokine and chemokine secretion in target organs. This, to the best of our knowledge, is the first report for testing the therapeutic effects of human CD8$^+$ Treg in vivo.

The major challenge of allogeneic BMT is to maintain long-term tolerance to allograft without compromising both general immunity and GVT activity. Our results showed that a rapid immune reconstitution and a high donor chimerism were achieved in humanized mice after treatment with CD8$^{hi}$ Treg. On day 100 post-transplantation, more than 80% of reconstituted human cells in peripheral blood, spleen, lung, liver and gut were originated from donor cells. In addition, the alloantigen-specific tolerance can be maintained up to 100 days after CD8$^{hi}$ Treg treatment. Taken together, these results demonstrated that CD8$^{hi}$ Treg induced a stable tolerance rather than simply eliminate responder cells. Furthermore, our data showed that CD8$^{hi}$ Treg treatment did not suppress the general immune function of co-transplanted conventional hPBMC against foreign antigen as evidenced by normal antigen-specific CD4$^+$ and CD8$^+$ T cell responses, and antibody production. Using a tumor-loaded humanized mice model, we also demonstrated that the GVT activity is preserved after the long-term tolerance induced by CD8$^{hi}$ Treg. Therefore, our study provided proof-of-concept of using ex vivo-induced human CD8$^{hi}$ Treg to control GVHD while preserving both general immunity and GVT activity after BMT. More importantly, we found that CD8$^{hi}$ Treg have direct cytotoxic activity against tumor cells, whereas the conventional CD4$^+$CD25$^+$ Treg do not have such anti-tumor activity, suggesting that CD8$^{hi}$ Treg may provide more advantage than CD4$^+$CD25$^+$ Treg to control GVHD and avoid tumor relapse (33).

Although some in vitro studies suggest IL-10, TGF-β, or CTLA-4 may be involved in the suppression of CD8$^+$ Treg (16, 17), it remains unknown whether these molecules participate in the suppression mediated by human CD8$^+$ Treg in vivo. Here, we found that the amount of IL-10 and TGF-β in target organs in humanized GVHD mice decreased after CD8$^{hi}$ Treg treatment, suggesting that IL-10 and TGF-β are not involved in the suppression in vivo. The indispensable role of CTLA-4 in the suppression of murine CD4$^+$Foxp3$^+$ Treg has been demonstrated in vitro and in vivo (7, 34, 35). By blocking CTLA-4 expression on CD8$^{hi}$ Treg, here we demonstrated that the suppression of alloeneic proliferative response by human CD8$^{hi}$ Treg in vitro and the prevention of acute GVHD by human CD8$^{hi}$ Treg in humanized mice are mediated mainly by CTLA-4. Consistent with that in murine CD4$^+$ Treg (35), here we found that blockade of CTLA-4 on human CD8$^{hi}$ Treg significantly increased the secretion of human IL-2 and TNF-α, and the accumulation of human CD3$^+$ T cells in lung, liver or gut, but did not affect the distribution of CD8$^{hi}$ Treg in these target organs during the progress of acute GVHD in humanized mice. In support of findings, other studies also showed that high level of IL-2 might favor the exacerbation of T cell-mediated inflammation rather than the survival of Treg under pro-inflammatory condition (36).

This study had some limitations. Similar to CD8$^+$ Treg reported by other groups (37, 38), human CD8$^{hi}$ Treg also have alloantigen-specific cytoxicity at a high ratio of Treg to target cells in vitro (23). Here, we also found that the blockade of CTLA-4 could not completely abolish the CD8$^{hi}$ Treg-mediated protection from acute GVHD. Therefore, we cannot exclude the possibility that the cytoxicity of CD8$^{hi}$ Treg may partially contribute to preventing acute GVHD in humanized mice. Since human non-haematopoietic cells also express MHC molecules, the profile of target cells in human GVHD should be broader than that in our model. To determine whether CD8$^{hi}$ Treg could also induce tolerance on non-haematopoietic cells, the solid organ transplantation models established in humanized mice could help evaluate the efficacy of CD8$^{hi}$ Treg-based therapy. In addition, although we demonstrated that the acute GVHD model established in this study is mediated mainly by human CD3$^+$ T cell-mediated allogeneic responses, we cannot completely exclude the involvement of xenogeneic responses in this GVHD model.

In summary, using humanized mice with a complete human immune system, we successfully established a novel human allogeneic acute GVHD model. Using this model, we demonstrated that human CD8$^{hi}$ Treg induced ex vivo by allogeneic hCD40-B cells can control acute GVHD in an allo-specific manner via reduction of alloreactive T cell proliferation and inflammatory cytokines secretion within target organs through a CTLA-4 dependent mechanism. Importantly, the CD8$^{hi}$ Treg not only can induce long-term tolerance effectively without compromising general immunity and GVT activity, but also have potent antitumor activity. Therefore, our study provided proof-of-concept of using ex vivo-induced human CD8$^{hi}$ Treg to control GVHD after BMT. This novel strategy could readily be extended to human clinical trials using human CD8$^{hi}$ Treg alone or in combination with minimal conventional immunosuppression to control GVHD. The GVHD model established here can also provide a more relevant platform for further studies of human immunopathogenesis and therapeutics for GVHD after BMT.

A highly efficient, low cost ex vivo system uses allogeneic CD40-activated B cells to induce and/or expand human antigen-specific Tregs on a large scale. The Tregs can be used treating immune related diseases, including GVHD. In one embodiment, the Tregs can be made with 50 ml or less activated B cells from a donor and 25 ml or less naïve T cells from the recipient to generate clinical grade Tregs. In another embodiment, the Tregs can be made with 25 ml or less activated B cells from a donor and 10 ml or less naïve T cells from the recipient. In yet another embodiment, the Tregs can be made with 10 ml or less activated B cells from a donor and 5 ml or less naïve T cells from the recipient.

Regulatory T cells are used in immunotherapy and for the inhibition/suppression of autoimmune responses, including GVHD. For example, one embodiment involves a method for inhibiting GVHD in a patient-recipient due to bone marrow transplantation, comprising obtaining a sample of naïve T cells from the donor of bone marrow; co-culturing B cells from the patient-recipient of bone marrow with naïve T cells from the donor in a suitable ratio in the absence of exogenous cytokines for a period of time sufficient to generate alloantigen-specific human regulatory T cells; and administering the alloantigen-specific human regulatory T cells to the patient-recipient of bone marrow.

Another embodiment involves a method for inhibiting a patient-recipient from rejecting tissue, cell, graft, or organ transplant from a donor due to an allogeneic rejection, comprising obtaining a sample of naïve T cells from the patient-recipient; co-culturing allogeneic B cells from the donor of tissue, cell, graft, or organ with naïve T cells from the patient-recipient in a suitable ratio in the absence of exogenous cytokines for a period of time sufficient to generate alloantigen-specific human regulatory T cells; and administering the alloantigen-specific human regulatory T cells to the patient-recipient of tissue, cell, graft, or organ transplant.

As used herein, "allogeneic cells" (allogenicity) are those isolated from one individual (the donor) and infused into another (the recipient or host); whereas "autologous cells" (antology) refer to those cells that are isolated and infused back into the same individual (recipient or host). The patient-recipient or host is typically a human host and the culture-expanded cells are human, although animals, including animal models for human disease states, are also included herein and therapeutic treatments of such animals are contemplated herein.

Yet another embodiment involves a method for preventing allergic asthma or airway hypersensitivity in a patient, comprising obtaining a sample of naïve T cells from the patient; co-culturing allergen-loaded B cells from the patient with their naïve T cells in a suitable ratio for a period of time sufficient to generate allergen-specific human regulatory T cells; and administering allergen-specific human regulatory T cells to the patient.

Also provided herein are methods to promote engraftment of human transplanted tissue, including whole or selected populations of bone marrow transplants, particularly by suppressing, inhibiting, blocking and/or preventing GVHD.

Further provided herein are methods for achieving an immunosuppressive effect in a patient comprising administering to the patient with an alloresponse or autoimmune response, an effective amount of Treg cells to achieve therapeutic suppression of the response. Alternatively, methods for achieving a preventative therapeutic effect in a patient involve administering to the patient, prior to onset of an alloresponse or autoimmune response, an effective amount of Treg cells to prevent the response. This method can be supplemented with preventing in vivo alloresponses or autoimmune responses in the patient by administering to the patient prior to the onset of the response, an effective amount of Treg cells, as described herein.

In any of the methods described herein, the Treg cells can be auto-reactive antigen-specific human $CD8^{hi}$ regulatory T cells. The auto-reactive antigen-specific human $CD8^{hi}$ regulatory T cells can contain $CD8^{hi}CD25^+Foxp3^+$ regulatory T cells.

One embodiment using specific cell types involves a method for inhibiting graft-versus-host disease (GVHD) in a patient-recipient due to bone marrow transplantation, comprising obtaining a sample of naïve $CD8^+CD25^-$ T cells from the donor of bone marrow; co-culturing CD40-activated B cells from the patient-recipient of bone marrow with naïve $CD8^+CD25^-$ T cells from the donor in a ratio of 1:10 in the absence of exogenous cytokines for a period of time sufficient to generate alloantigen-specific human $CD8^{hi}$ regulatory T cells; and administering the alloantigen-specific human $CD8^{hi}$ regulatory T cells to the patient-recipient of bone marrow.

Another embodiment involves a method for inhibiting a patient-recipient from rejecting tissue, cell, graft, or organ transplant from a donor due to an allogeneic rejection, comprising obtaining a sample of naïve $CD8^+CD25^-$ T cells from the patient-recipient; co-culturing allogeneic CD40-activated B cells from the donor of tissue, cell, graft, or organ with naïve $CD8^+CD25^-$ T cells from the patient-recipient in a ratio of 1:10 in the absence of exogenous cytokines for a period of time sufficient to generate alloantigen-specific human $CD8^{hi}$ regulatory T cells; and administering the alloantigen-specific human $CD8^{hi}$ regulatory T cells to the patient-recipient of tissue, cell, graft, or organ transplant.

Yet another embodiment involves a method for preventing allergic asthma or airway hypersensitivity in a patient, comprising obtaining a sample of naïve $CD8^+CD25^-$ T cells from the patient; co-culturing allergen-loaded CD40-activated B cells from the patient with their naïve $CD8^+CD25^-$ T cells in a ratio of 1:10 for a period of time sufficient to generate allergen-specific human $CD8^{hi}$ regulatory T cells; and administering allergen-specific human $CD8^{hi}$ regulatory T cells to the patient.

Also, contemplated herein are methods for preventing autoimmune diseases in a patient comprising: (a) Systemic Rheumatic diseases [(1) Systemic lupus erythematosus; (2) Progressive systemics clerosia; (3) Chronic discoid lupus; (4) Mixed connective tissue disease (MCTD)] (b) Rheumatoid Arthritis; (c) Kidney diseases resulting from reaction of antibodies with renal basement membrane, or the formation of circulating immune complex glomeraionephritis; (d) Hashmotos disease (chronic thyroiditis); (e) Diseases involving antibodies to tissue specific antigens [1. Mitrochrondrial antigens (antibodies found in primary biliary cirrhosis). 2. Smooth muscle antigens, i.e., antibodies which may be demonstrated in some infectious disease such as viral hepatitis, yellow fever and infectious mononucleosis and in some malignancies such as carcinoma of the ovary and malignant melanoma and in some types of cirrhosis. Gastric Parietal Cells—antibodies to intracytoplasmic antigens of gastric parietal cells, to the B12 binding site of intrinsic factor and to the intrinsic factor B12 complex may be found in patients with pernicious anemia.] (f) Skin Diseases [1. Vesiculoballous skin diseases-pemphigus, pemphigoids, dermatitis herpeti formis, herpes gestatenis; 2. Cutaneous forms of lupus erythematosis vasculitis (rheumatoid vasculitis)], and (g) Human sperm antibodies. The methods involve obtaining a sample of naïve $CD8^+CD25^-$ T cells from the patient; co-culturing auto-reactive antigen-loaded CD40-activated B cells from the patient with their naïve $CD8^+CD25^-$ T cells in a ratio of 1:10 for a period of time sufficient to generate auto-reactive antigen-specific human $CD8^{hi}$ regulatory T cells; and administering auto-reactive antigen-specific human $CD8^{hi}$ regulatory T cells to patient.

In any of the methods described herein, the patient-recipient-host can be treated prior to, at the time of, and/or immediately after tissue transplantation. An advantage associated with the methods described herein is that a relatively low number of doses can be administered to induce long term antigen-specific tolerance while preserving general functions of the reinstituted immune system in recipients. For example, methods described herein can involve 10 or fewer administrations of the Tregs. In another example, methods described herein can involve 5 or fewer administrations of the Tregs. In yet another example, methods described herein can involve 2 or fewer administrations of the Tregs. In still yet another example, methods described herein can involve one administration of the Tregs.

Since the Tregs used herein are recipient specific, an advantage in some instances is that it is unnecessary to use a donor with good human leukocyte antigens (HLA) match for the patient-recipient. That is, HLA-matching can become an unnecessary factor in transplantation procedures.

With respect to any figure or numerical range for a given characteristic, a figure or a parameter from one range may be combined with another figure or a parameter from a different range for the same characteristic to generate a numerical range. Other than in the operating examples, or where otherwise indicated, all numbers, values and/or expressions referring to quantities of ingredients, reaction conditions, etc., used in the specification and claims are to be understood as modified in all instances by the term "about."

EXPERIMENTAL RESULTS

Unless otherwise indicated in the following examples and elsewhere in the specification and claims, all parts and percentages are by weight, all temperatures are in degrees Centigrade, and pressure is at or near atmospheric pressure. Establishment of a Human Allogeneic Acute GVHD Model in Humanized Mice.

Figure 1B:
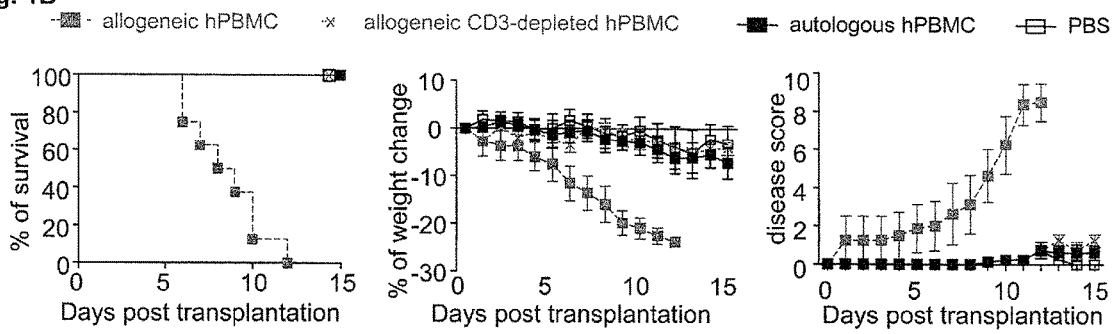
Figure 1C:
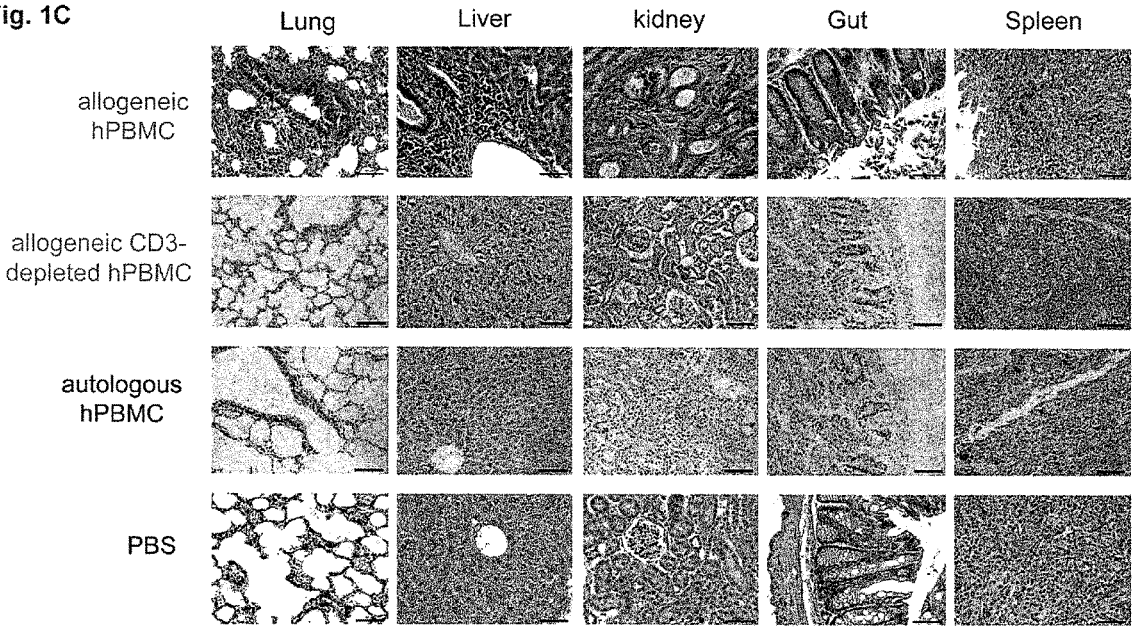

To mimic GVHD in humans after BMT, we established a human allogeneic acute GVHD model by injection of 1.0× $10^7$ allogeneic donor hPBMC into humanized mice with stable reconstitution of recipient hPBMC (FIG. 1A). Acute lethal GVHD was observed in humanized mice receiving allogeneic donor hPBMC, as evidenced by weight loss, disease score (hunching, activity, ruffling and diarrhea) (27) and death during 1-2 weeks after transplantation (FIG. 1B). Similar to humans (28), humanized mice with GVHD showed severe inflammation, leukocyte infiltration, fibrosis, necrosis and tissue damage in target organs such as lung, liver, kidney, gut and spleen (FIG. 1C). In contrast, injection of the same amount of either autologous hPBMC or $CD3^+$ T-cell-depleted allogeneic hPBMC into humanized mice failed to induce acute GVHD (FIGS. 1B, 1C). These results indicated that the acute GVHD induced by allogeneic donor hPBMC in humanized mice was mediated mainly by donor T cells.

Figure 1D:
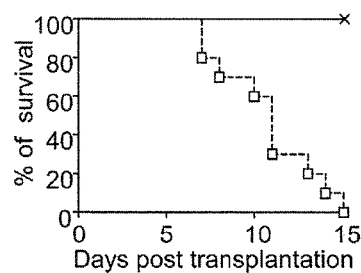
Figure 1E:
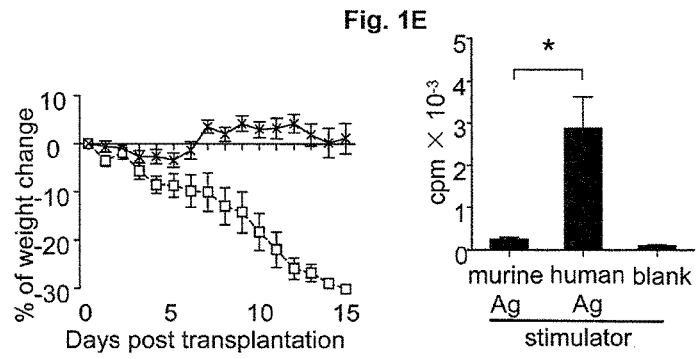

Different from that in humanized mice, injection of the same amount of donor hPBMC into $Rag2^{-/-}\gamma c^{-/-}$ mice caused only minor weight loss (around 2%) without death (FIG. 1D), suggesting no significant xenogeneic response was involved in this acute GVHD model. No proliferative response of donor hPBMC to xenogeneic murine antigen was also observed in vitro (FIG. 1E). To further exclude potential influences of exogeneic responses, we generated $A2^+$ and $A2^-$ humanized mice with hPBMC from $HLA-A2^+$ and $HLA-A2^-$ donors respectively. We then isolated $A2^+$ human T cells from the spleen and blood of $A2^+$ humanized mice and used them as the stimulant to induce GVHD in $A2^-$ humanized recipient mice (FIG. 2A). These $A2^+$ allogeneic human T cells remained stably engrafted in $Rag2^{-/-}\gamma c^{-/-}$ mice for at least four weeks: we subsequently refer to this as an "education" process and to the engrafted T cells as educated human $CD3^+$ ($A2^+$ $eduCD3^+$) T cells like hPBMC, purified $A2^+$ $eduCD3^+$ T cells showed no proliferative responses to xenogeneic murine antigen while maintaining their responses to human alloantigens (FIG. 2B). Importantly, allogeneic $A2^+$ $eduCD3^+$ T cells induced a lethal acute GVHD in $A2^-$ humanized recipient mice but not in $Rag2^{-/-}\gamma c^{-/-}$ mice, just as conventional human $CD3^+$ T cells did from the same $A2^+$ donors (FIG. 2C). These results demonstrated that the acute GVHD model established here is mediated mainly by human $CD3^+$ T cell-mediated allogeneic responses but not by xenogeneic responses.

$CD8^{hi}$ Treg Suppress the Activation and Proliferation of Alloreactive T Cells In Vitro.

Figure 3A:
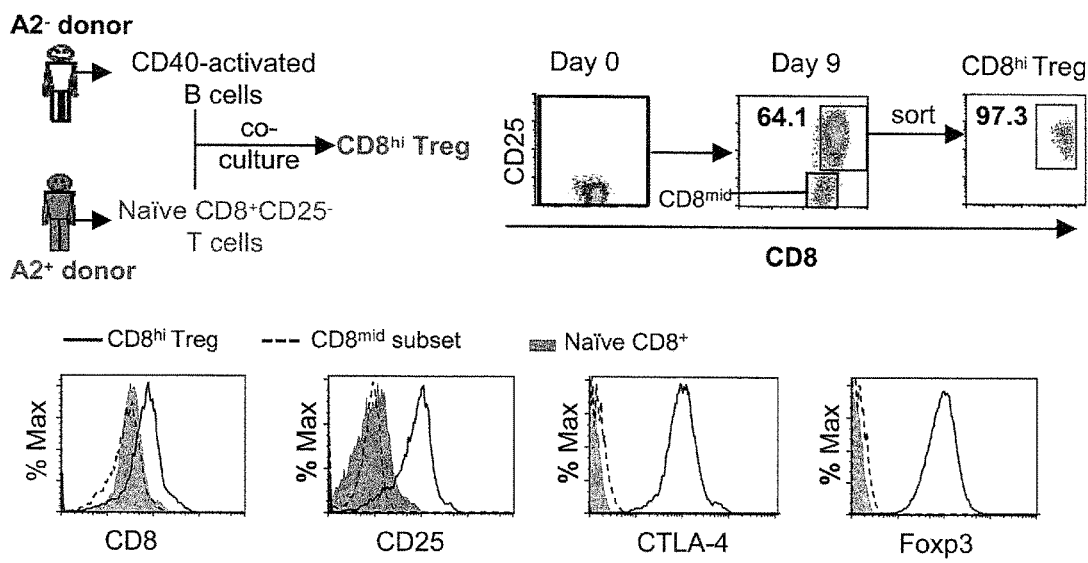
FIGS. 3A-3D depict data demonstrating that the concentration of human TGF-β and IL-10 does not increase in the target organs of $CD8^{hi}$ Treg-treated humanized GVHD mice.
Figure 3B:
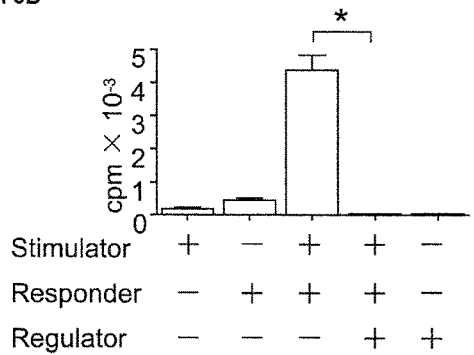
Figure 3C:
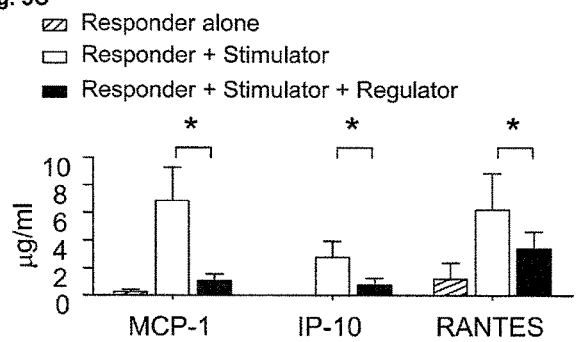
Figure 3D:
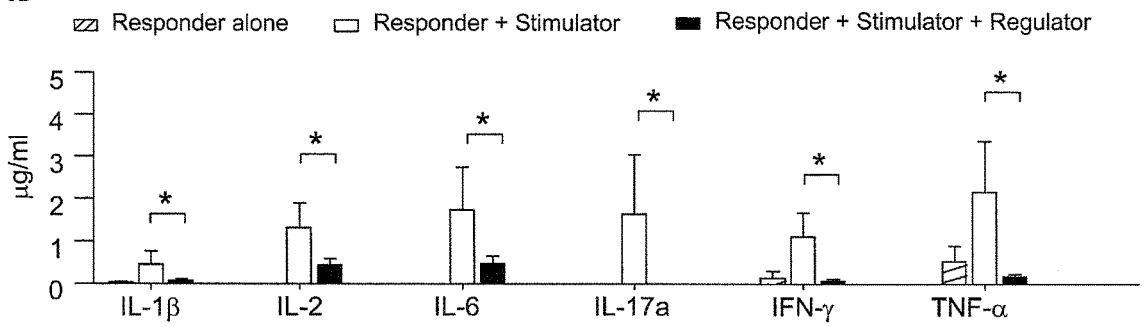

We then generated human $CD8^{hi}$ Treg according to the protocol we described previously (23). Human CD40-activated B (hCD40-B) cells were generated from $A2^-$ B cells ($A2^-$ donor) in large scale by activation and expansion through engagement of CD40 using CD40-ligand transfected murine fibroblast cell line (NIH3T3-CD40L). Highly purified naïve $CD8^+CD25^-$ T cells from $A2^+$ donors were then co-cultured with these allogeneic $A2^-$ hCD40-B cells (23). On day 9 of co-culture, $CD8^{hi}$ Treg with high level of CD25, CTLA-4 and Foxp3 expression were induced and then purified by FACS (FIG. 3A). As shown in FIG. 3B, the purified $CD8^{hi}$ Treg potently suppressed the proliferation of autologous hPBMC stimulated by irradiated allogeneic hPBMC in vitro. Moreover, $CD8^{hi}$ Treg significantly inhibited the secretion of inflammatory chemokines (MCP-1, IP-10, and RANTES) and cytokines (IL-1β, IL-2, IL-6, IL-17a, IFN-γ, and TNF-α) by autologous hPBMC (FIGS. 3C, 3D). With intracellular cytokine staining, $CD8^{hi}$ Treg were further found to suppress the expression of IFN-γ, TNF-α, and IL-2 in autologous $CD4^+$ T cells significantly but only showed a similar suppressive effect on IFN-γ expression in autologous $CD8^+$ T cells during initial 24 hours of co-culture (FIG. 1). These results indicated that $CD8^{hi}$ Treg induced by hCD40-B inhibit the activation and proliferation of alloreactive T cells in vitro.

$CD8^{hi}$ Treg Inhibit Acute GVHD in an Allo-Specific Manner In Vivo.

Figure 4A:
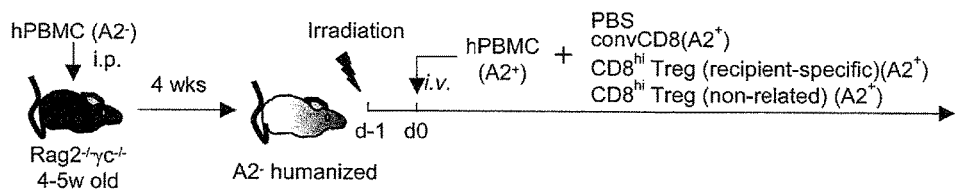
FIGS. 4A-4E depict a model including illustrating the effects of $CD8^{hi}$ Treg on inflammatory cytokine production by $CD4^+$ and $CD8^+$ T cells from donor PBMC in vivo.
Figure 4B:
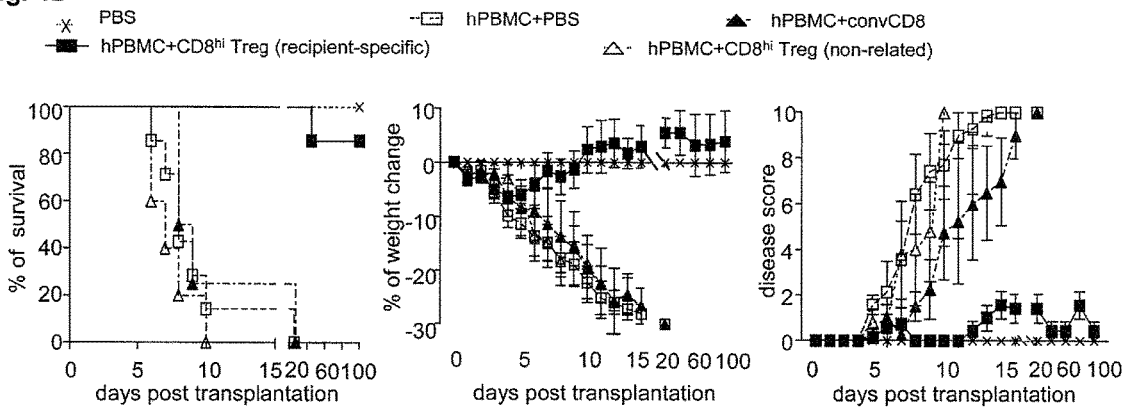
Figure 4C:
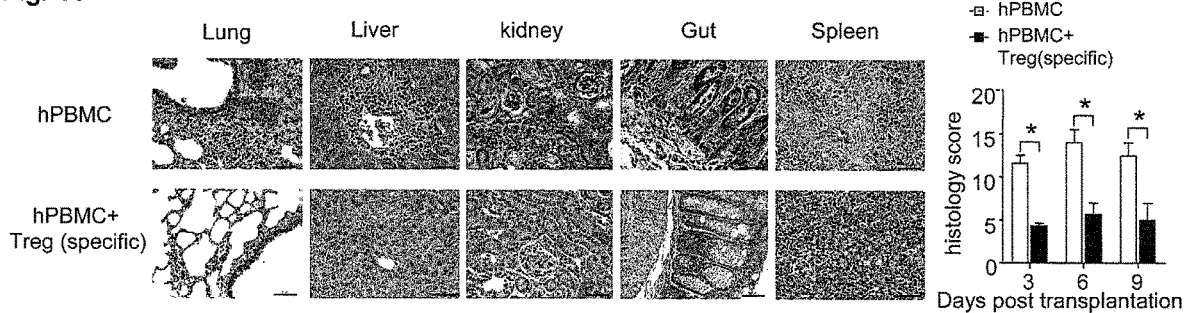
Figure 4D:
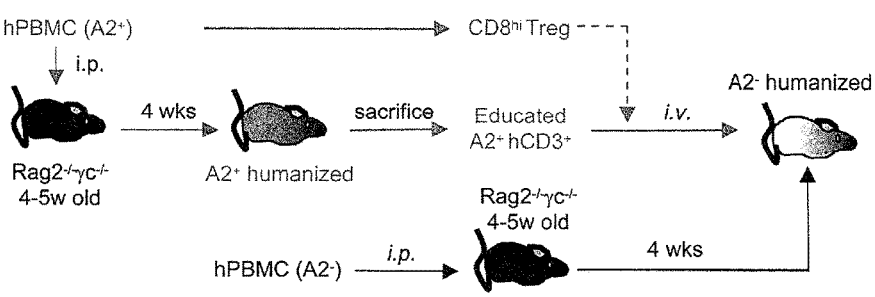
Figure 4E:
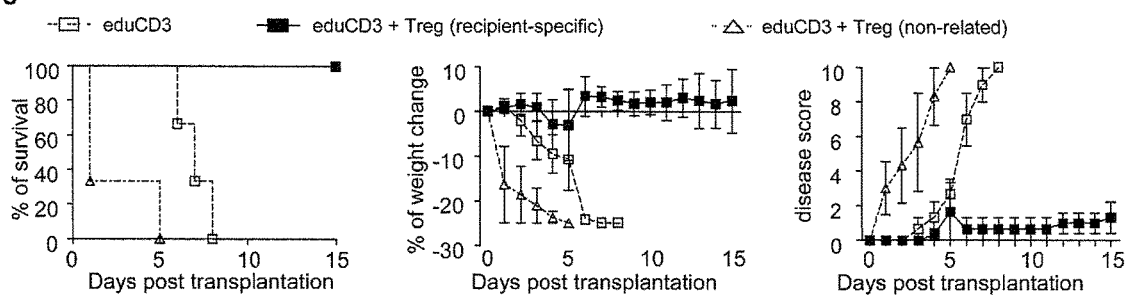

To evaluate the in vivo effects and antigen-specificity of these ex vivo-induced $CD8^{hi}$ Treg, recipient-specific $A2^+$ $CD8^{hi}$ Treg were induced by hCD40-B cells from a $A2^-$ donor whose hPBMC were used for establishing the humanized recipient mice. Non-related $A2^+$ $CD8^{hi}$ Treg were induced by $A2^-$ hCD40-B cells from a third party. Highly purified (>97% purity) $1.0 \times 10^6$ non-related $A2^+$ $CD8^{hi}$ Treg, recipient-specific $A2^+$ $CD8^{hi}$ Treg or conventional $A2^+$ $CD8^+$ T cells were transplanted with $1.0 \times 10^7$ autologous $A2^+$ hPBMC into $A2^-$ humanized recipient mice (FIG. 4A). As shown in FIG. 4B, adoptive transfer of recipient-specific $A2^+$ $CD8^{hi}$ Treg not only significantly ameliorated the severity of acute GVHD in terms of weight loss and disease score, but also protected mice from death during 100 days of observation. Moreover, recipient-specific $A2^+$ $CD8^{hi}$ Treg prevented leukocyte infiltration and reduced pathology in lung, liver, gut, kidney and spleen on day 6 post-transplantation (FIG. 4C). In contrast, neither non-related $A2^+$ $CD8^{hi}$ Treg nor conventional $A2^+$ $CD8^+$ T cells had such protective effects (FIG. 4B). Importantly, the antigen-specific protection of $CD8^{hi}$ Treg was also confirmed in an acute GVHD model induced by allogeneic $eduCD3^+$ T cells (FIGS. 4D, 4E). Collectively, these results demonstrated that $CD8^{hi}$ Treg inhibit human allogeneic acute GVHD in an allo-specific manner in vivo.

$CD8^{hi}$ Treg Inhibit Alloreactive T-Cell Proliferation and Inflammatory Chemokine/Cytokine Secretion.

To investigate the mechanisms underlying the prevention of GVHD by $CD8^{hi}$ Treg, allogeneic donor hPBMC ($A2^+$) labeled with a lipophilic dye (Dil) were injected into $A2^-$ humanized recipient mice with $A2^+$ recipient-specific donor $CD8^{hi}$ Treg that were distinguished using another lipophilic dye (Dir). Organ imaging ex vivo detected hPBMC and $CD8^{hi}$ Treg in lung and liver only, where their distribution overlapped (FIG. 5A). After transplantation, the accumulation of donor hPBMC in these two organs gradually increased to peak levels on day 6 and then decreased on day 9 (FIG. 5A, FIG. 2A). The treatment of $CD8^{hi}$ Treg significantly reduced the accumulation of allogeneic hPBMC in target organs from day 1 to day 9 post-transplantation (FIG. 5B, FIG. 2A). Injection of CFSE-labeled allogeneic donor hPBMC ($A2^+$) into $A2^-$ humanized recipient mice, we further found that $CD8^{hi}$ Treg treatment significantly inhibited the proliferation of donor $hCD3^+$ T cells ($A2^+$) in these target organs in vivo from day 3 to day 9 post-transplantation (FIG. 5C, FIG. 2B). Furthermore, $CD8^{hi}$ Treg treatment significantly inhibited the secretion of human inflammatory chemokines and cytokines, such as RANTES (CCL5), IP-10 (CXCL10), MCP-1 (CCL1), IL-1β, IL-2, IL-6, IL-17A, IFN-γ, and/or TNF-α from lung, liver or gut on day 6 post-transplantation (FIGS. 5D, 5E), whereas the amount of IL-10 and TGF-β in target organs was actually lower from day 3 to day 9 day after CD8$^{hi}$ Treg treatment in humanized mice compared with mice receiving hPBMC only (FIG. 3). Specifically, the percentages of IFN-γ-, TNF-α- or IL-2-secreting CD4 and CD8 T cells in the lung and liver were significantly decreased in the humanized recipient mice after treatment of CD8$^{hi}$ Treg (FIG. 4). These results demonstrated that CD8$^{hi}$ Treg ameliorate human allogeneic acute GVHD by reduction of alloreactive T-cell proliferation and inflammatory chemokine and cytokine secretion in target organs.

The Prevention of Acute GVHD by CD8$^{hi}$ Treg is Dependent on CTLA-4.

Figure 6A:
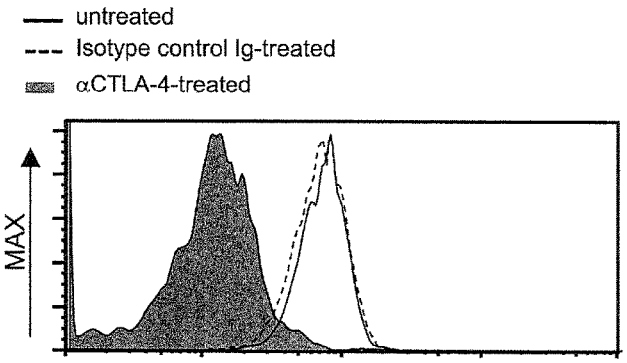
FIGS. 6A-6F depict graphical illustrations of molecular mechanisms of $CD8^{hi}$ Treg-mediated cytotoxicity against allogeneic LCL.
Figure 6B:
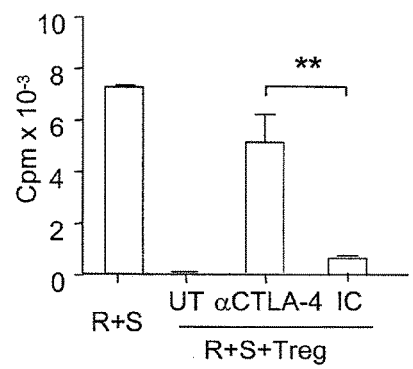
Figure 6C:
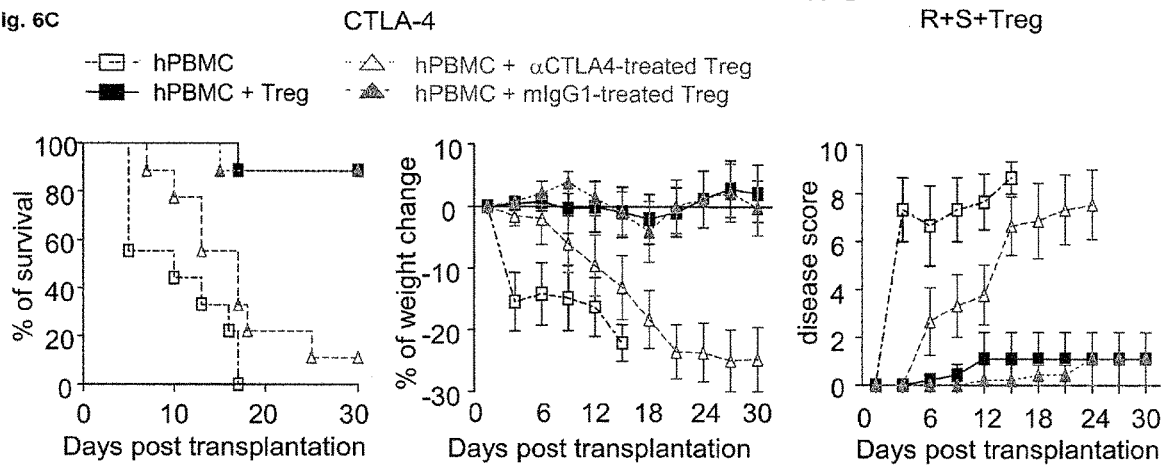
Figure 6D:
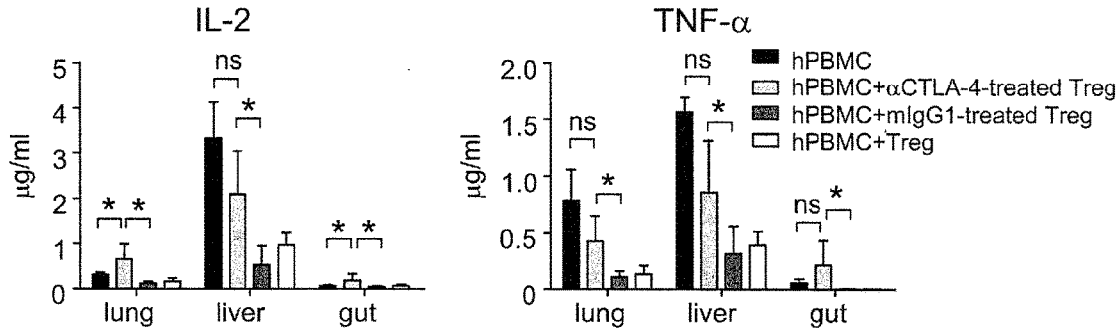
Figure 6E:
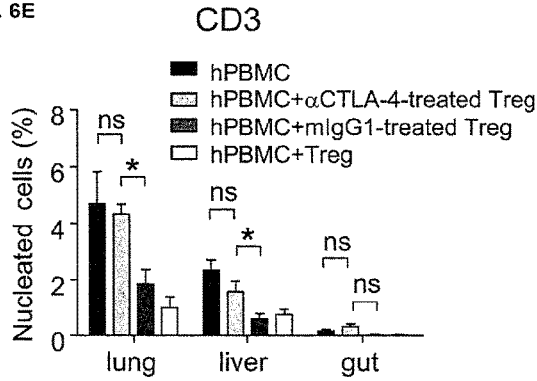
Figure 6F:
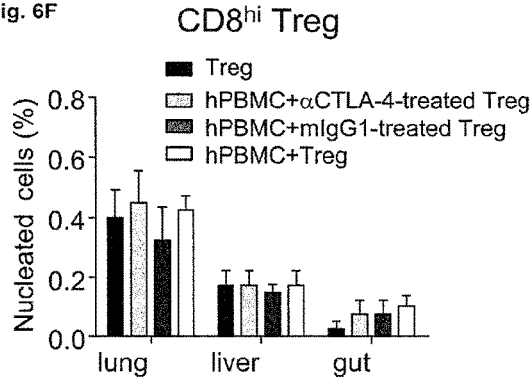

As CD8$^{hi}$ Treg express high level of CTLA-4 (FIG. 3A), we further determined whether the control of acute GVHD is mediated by CTLA-4. With pre-treatment of CTLA-4 neutralizing antibody, the expression of CTLA-4 on CD8$^{hi}$ Treg was completely blocked (FIG. 6A). The suppression of the allogeneic proliferative response by CD8$^{hi}$ Treg was also significantly reversed after pre-treatment with CTLA-4 neutralizing antibody in vitro (FIG. 6B). Importantly, blockade of CTLA-4 expression on CD8$^{hi}$ Treg abolished their protection from acute GVHD in humanized mice in terms of mice survival, weight loss and disease score (FIG. 6C). Moreover, blockade of CTLA-4 on CD8$^{hi}$ Treg significantly reversed their suppression on the production of human IL-2 and TNF-α, and the accumulation of hCD3$^+$ T cells in lung, liver or gut, but did not affect the distribution of CD8$^{hi}$ Treg in these target organs on day 6 post-transplantation (FIGS. 6D, 6E, 6F). These results indicated the prevention of acute GVHD by CD8$^{hi}$ Treg in humanized mice is mediated mainly by CTLA-4.

CD8$^{hi}$ Treg Induce Long-Term Tolerance and Preserve General Immunity.

Figure 7A:
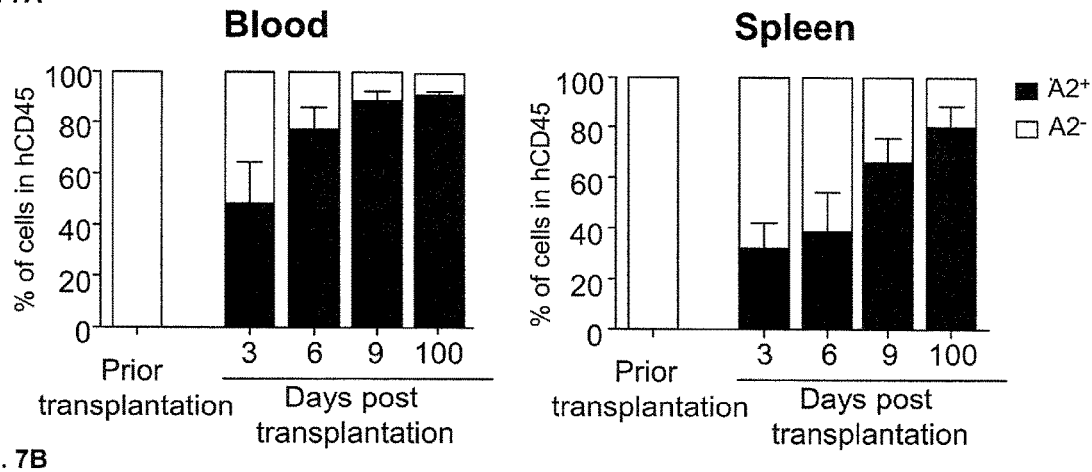
FIGS. 7A-7D depict data demonstrating that recipient-specific donor $CD8^{hi}$ Treg induces long-term tolerance and preserves general immunity in humanized mice.
Figure 7B:
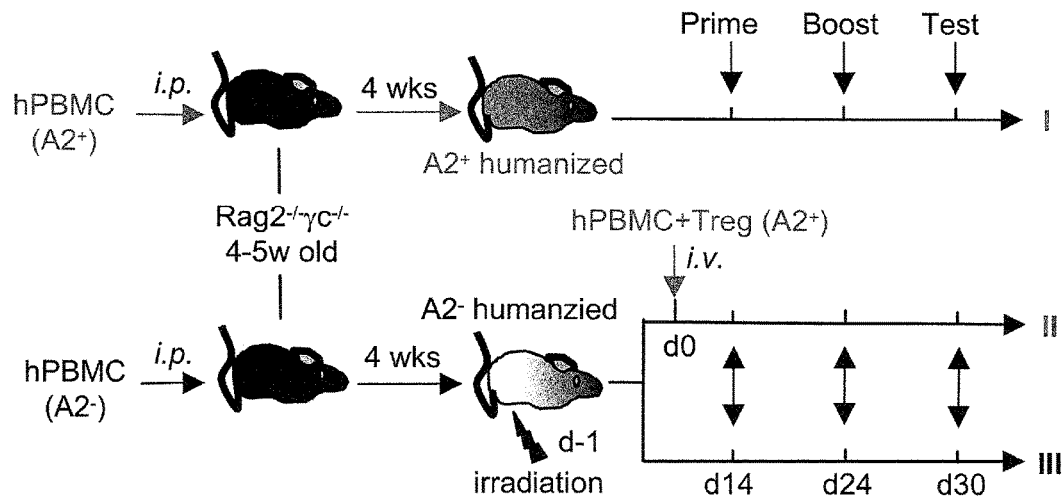
Figure 7C:
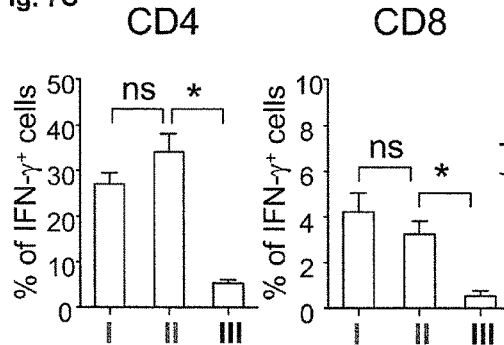
Figure 7D:
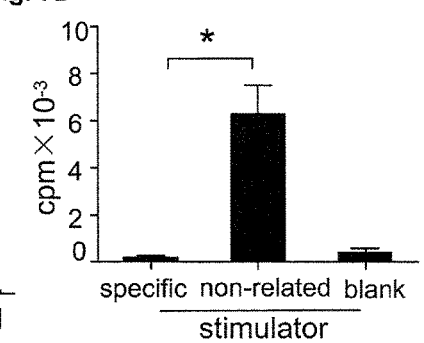

To monitor chimerism of donor- and recipient-original cells, hPBMC and CD8$^{hi}$ Treg from A2$^+$ donor were injected into humanized recipient mice reconstituted with A2$^-$ hPBMC. As shown in FIG. 7A, a mix chimerism was established in A2$^-$ humanized recipient mice within 9 days post transplantation of hPBMC and CD8$^{hi}$ Treg. On day 100, most reconstituted lymphoid cells in A2$^-$ humanized recipient mice were originated from A2$^+$ donor in peripheral blood, spleen, lung, liver and gut after treatment with CD8$^{hi}$ Treg (FIG. 7A, FIG. 5). We then further examined the general immune function in A2$^-$ humanized recipient mice after 14 days of post-transplantation with A2$^+$ hPBMC and CD8$^{hi}$ Treg by immunization with tetanus toxoid (TT) vaccine (FIG. 7B). As shown in FIG. 7C, the vaccination induced TT-specific IFN-γ secretion by human CD4$^+$ and CD8$^+$ T cells and serum TT-specific human antibody in CD8$^{hi}$ Treg-treated humanized recipient mice (group II) (FIG. 7C). Importantly, the T-cell responses and antibody production in these mice were comparable with those in humanized mice reconstituted with hPBMC from the same donor (group I) (FIG. 7C). Moreover, Donor-origin CD3$^+$ T cells isolated from CD8$^{hi}$ Treg-treated humanized recipient mice on day 100 did not respond to recipient antigen but had a robust proliferative response to non-related antigens from a third party (FIG. 7D), indicating that the alloantigen-specific tolerance can be maintained up to 100 days after a single dose of CD8$^{hi}$ Treg treatment. These results demonstrated that CD8$^{hi}$ Treg can induce long-term tolerance and retain general immune function to foreign antigens in humanized recipient mice.

Figure 8A:
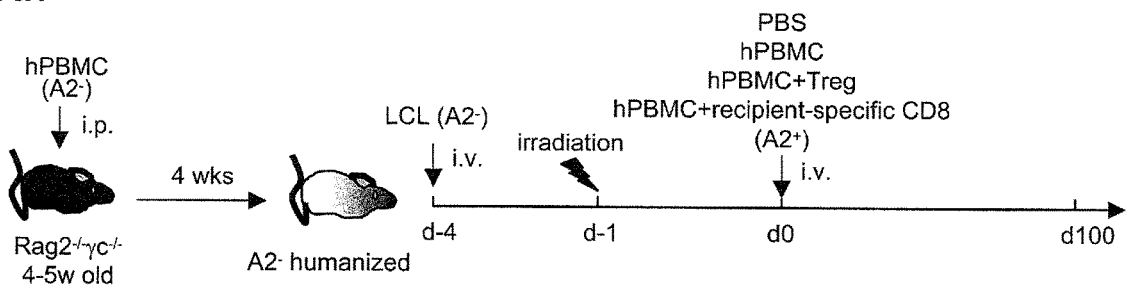
FIGS. 8A-8D depict graphical illustrations of graft-versus-tumor (GVT) activity in humanized GVHD mice after treatment.
Figure 8B:
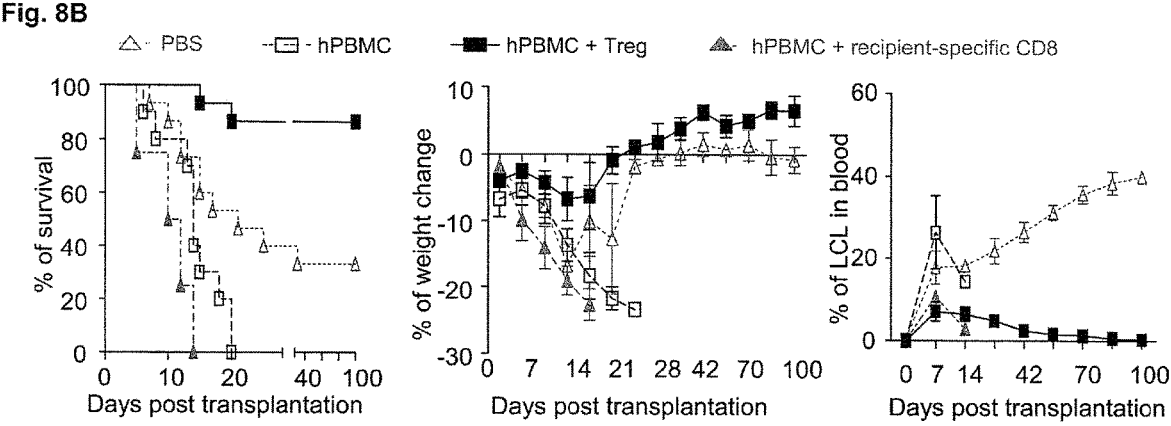
Figure 8C:
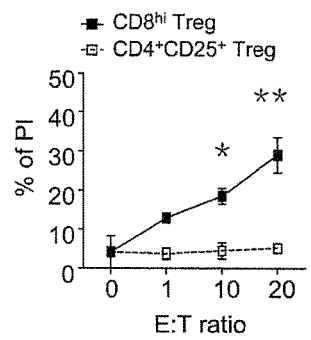
Figure 8D:
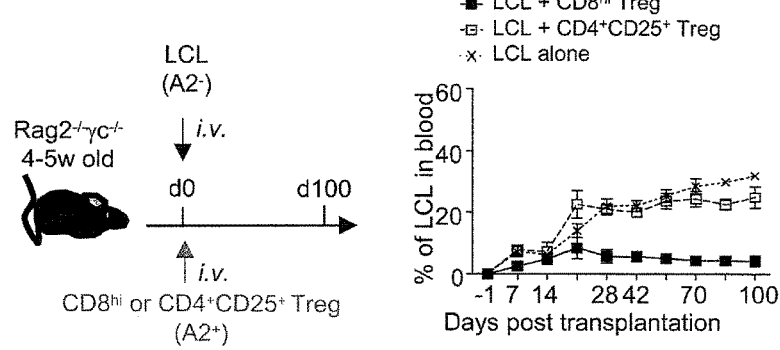

To further determine whether the treatment of CD8$^{hi}$ Treg affects GVT activity, humanized mice were injected intravenously (i.v.) with 1×10$^5$ GFP-expressing Epstein Barr virus (EBV)—transformed autologous lymphoblastoid cell line (LCL) cells four days before transplantation of 1×10$^7$ donor hPBMC with or without 1×10$^6$ recipient-specific donor CD8$^{hi}$ Treg or recipient-specific CD8$^+$ T cells (FIG. 8A). All mice that received donor hPBMC alone, or donor hPBMC and recipient-specific CD8$^+$ T cells died, whereas steady LCL cell growth was seen in the mice treated with PBS. In contrast, around 90% of humanized mice that received donor hPBMC and recipient-specific donor CD8$^{hi}$ Treg survived, with neither detectable tumor cells in peripheral blood (FIG. 8B) nor visible solid tumor during the observation of 100 days after transplantation. These results demonstrated that GVT response is preserved after the long-term tolerance induced by CD8$^{hi}$ Treg. Interestingly, CD8$^{hi}$ Treg exhibited direct cytotoxic activity against LCL cells both in vitro and in vivo, whereas the CD4$^+$CD25$^+$ Treg expanded by anti-CD3/CD28 antibodies had no such cytotoxicity against LCL cells (FIGS. 8C, 8D). The cytotoxicities of CD8$^{hi}$ Treg were mediated by Fas-FasL and perforin-Granzyme B pathways because either blockade of FasL, inhibition of perforin, or inactivation of granzyme B could significantly abrogated their cytotoxicities (FIG. 6).

FIGS. 1A-1E relate to the establishment of a human allogeneic GVHD model in humanized mice. (FIG. 1A) Protocol for establishment of GVHD model. Rag2$^{-/-}$γc$^{-/-}$ mice were injected with hPBMC. After 4 weeks, humanized mice with stable reconstitution of hPBMC were established. Humanized mice were then irradiated sublethally and transplanted with autologous hPBMC, allogeneic hPBMC, CD3-depleted allogeneic hPBMC, or PBS. (FIG. 1B) Survival, weight change, disease score in humanized mice (allogeneic hPBMC vs. PBS, autologous hPBMC or CD3-depleted allogeneic hPBMC, p<0.001; PBS vs. CD3-depleted allogeneic hPBMC or autologous hPBMC, p>0.05. n=8 per group). Data represent 3 independent experiments. (FIG. 1C) Representative histology of the target organs harvested on day 6 post-transplantation. (FIG. 1D) Survival and weight change of humanized or Rag2$^{-/-}$γc$^{-/-}$ mice after transplantation of allogeneic hPBMC (n=10 per group). Data represent 3 independent experiments. (FIG. 1E) Proliferation of donor hPBMC against irradiated spleen cells of Rag2$^{-/-}$γc$^{-/-}$ mice (mouse Ag) or recipient hPBMC (human Ag). Data are shown as mean±SEM and represent 3 independent experiments (*p<0.05).

FIGS. 2A-2C relate to human allogeneic GVHD induced by educated CD3$^+$ T cells in humanized mice. (FIG. 2A) Humanized mice were reconstituted with hPBMC from human donor of HLA-A2+(A2$^+$) or HLA-A2$^-$ (A2$^-$). Four weeks later, human educated A2$^+$ CD3$^+$ T cells (hCD3$^+$) were isolated from the peripheral blood and spleen of A2$^+$ humanized mice. GVHD was induced in A2$^-$ humanized mice using allogeneic educated A2$^+$ hCD3$^+$ or conventional A2$^+$ hCD3$^+$ T cells from A2$^+$ donor. (FIG. 2B) Proliferation of conventional human CD3$^+$ (conCD3$^+$) and educated CD3$^+$ (eduCD3$^+$) T cells from A2$^+$ donor against irradiated spleen cells of Rag2$^{-/-}$γc$^{-/-}$ mice (murine Ag) or A2$^-$ hPBMC (human Ag). Data are shown as mean±SEM and represent 3 independent experiments. (FIG. 2C) Survival and weight change of A2$^-$ humanized mice receiving conventional A2$^+$ hCD3$^+$ (group 1) or educated A2$^+$ hCD3$^+$ (group 4) T cells, and Rag2$^{-/-}$γc$^{-/-}$ mice receiving conventional A2$^+$ hCD3$^+$ (group 2) or educated A2$^+$ hCD3$^+$ (group 3) T cells (n=6 per group). For survival and weight change, group 1 vs. group 2 or group 3, p<0.001; group 4 vs. group 2 or group 3, p<0.001; group 1 vs. group 4, p>0.05. Data shown here represent 3 independent experiments.

FIGS. 3A-3D describe CD8$^{hi}$ Treg suppressing the activation and proliferation of alloreactive T cells in vitro. (FIG.

3A) Protocol of induction and purification of $CD8^{hi}$ Treg. $CD8^{hi}$ Treg were induced from naïve $CD8^+CD25^-$ T cells ($A2^+$ donor) by co-culture with allogeneic hCD40-B cells ($A2^-$ donor) for 9 days. The surface expression of CD8, CD25, CTLA-4, and intracellular expression of Foxp3 in naïve $CD8^+$ T cells, $CD8^{hi}$ Treg and $CD8^{mid}$ subset were detected by flow cytometry. (FIG. 3B) Effect of donor $CD8^{hi}$ Treg (Regulator) on the proliferation of donor hPBMC (Responder) to irradiated recipient hPBMC (Stimulator). Data shown here represented means±SEM of 4 replicates (*$p<0.05$). (FIGS. 3C, 3D) Donor $CD8^{hi}$ Treg (Regulator) were co-cultured with donor hPBMC (Responder) and irradiated recipient hPBMC (Stimulator) for 24 hours. The concentrations of inflammatory chemokines (FIG. 3C) and cytokines (FIG. 3D) in the supernatant were measured. Data shown as means±SEM represent 4 independent experiments (*$p<0.05$).

FIGS. 4A-4E illustrate $CD8^{hi}$ Treg inhibiting human allogeneic acute GVHD in an allo-specific manner in vivo. (FIG. 4A) Non-related or recipient-specific donor $CD8^{hi}$ Treg ($A2^+$) were induced by hCD40-B cells from a third party (non-related) donors or those whose hPBMC ($A2^-$) were used for establishing humanized recipient mice respectively. Non-related $CD8^{hi}$ Treg, recipient-specific $CD8^{hi}$ Treg, or conventional $CD8^+$ T cells (convCD8) were transplanted with hPBMC from same $A2^+$ human donors into $A2^-$-humanized recipient mice. Survival, weight change, disease score (FIG. 4B), representative histology and histology score of target organs (lung, liver, kidney and gut) on day 6 post-transplantation (FIG. 4C) in $A2^-$-humanized recipient mice are shown. For survival, weight change and disease score: hPBMC+$CD8^{hi}$ Treg (recipient-specific) vs. hPBMC+PBS, hPBMC+$CD8^{hi}$ Treg (non-related) or hPBMC+convCD8, $p<0.001$. hPBMC+PBS (n=7); hPBMC+$CD8^{hi}$ Treg (recipient-specific) (n=7); hPBMC+$CD8^{hi}$ Treg (non-related) (n=5); hPBMC+convCD8 (n=4); untreated (n=4). *$p<0.05$. (FIG. 4D) Protocol for inhibiting educated $CD3^+$ T cells-mediated human allogeneic GVHD by $CD8^{hi}$ Treg. (FIG. 4E) Survival, weight change, and disease score in $A2^-$-humanized recipient mice receiving educated $A2^+hCD3^+$ T cells (eduCD3) alone or educated $A2^+CD3^+$T cells and recipient-specific or non-related $CD8^{hi}$ Treg (n=6 per group). For survival, weight change, and disease score, eduCD3+Treg (recipient-specific) v.s. eduCD3 or eduCD3+Treg (non-related), $p<0.0001$. Data represent 3 independent experiments.

FIGS. 5A-5E show recipient-specific donor $CD8^{hi}$ Treg suppress alloreactive T-cell proliferation and inflammatory chemokine and cytokine secretion in target organs after donor hPBMC transplantation. (FIGS. 5A, 5B) Distribution of hPBMC (Dil-labeled, green) and $CD8^{hi}$ Treg (Dir-labeled, red) (FIG. 5A), accumulation of donor hPBMC (shown as intensity of Dil signal) (FIG. 5B) in target organs on day 6 post-transplantation in humanized GVHD mice with or without recipient-specific donor $CD8^{hi}$ Treg treatment. Data are representative of four independent experiments. (FIG. 5C) Proliferation of donor $CD3^+$ T cells determined by CFSE staining (original histogram represents for the expression level of CFSE in donor $CD3^+$ T cells before injection into recipient) in target organs on day 6 post-transplantation in humanized GVHD mice with or without recipient-specific donor $CD8^{hi}$ Treg treatment. Data represent 4 independent experiments. (FIGS. 5D, 5E) Concentration of inflammatory chemokines (FIG. 5D) and cytokines (FIG. 5E) in lungs, livers, and guts on day 6 post-transplantation in humanized mice with or without recipient-specific donor $CD8^{hi}$ Treg treatment. Data are shown as mean±SEM and represent 4 independent experiments (*$p<0.05$).

FIGS. 6A-6F depict the prevention of acute GVHD by recipient-specific donor $CD8^{hi}$ Treg depends on CTLA-4. (FIG. 6A) Expression level of CTLA-4 on $CD8^{hi}$ Treg pre-treated with CTLA-4 neutralizing mAb or isotype control (mIgG1). (FIG. 6B) Effect of CTLA-4 blockade on the suppression by $CD8^{hi}$ Treg on allogeneic proliferative responses. Untreated $CD8^{hi}$ Treg (UT), $CD8^{hi}$ Treg pre-treated with CTLA-4 neutralizing mAb (αCTLA-4) or its isotype control (IC, mIgG1) were added to co-culture of donor hPBMC (R, responder) and irradiated recipient hPBMC (S, stimulator). (FIG. 6C) $CD8^{hi}$ Treg pre-treated with CTLA-4 neutralizing mAb (αCTLA-4) or mIgG1 were transplanted with allogeneic hPBMC into humanized mice. Survival, weight change, disease score in humanized mice are shown (n=6 per group). For survival, weight change and disease score: hPBMC+Treg or hPBMC+mIgG1-treated-Treg vs. hPBMC or hPBMC+αCTLA-4-treated Treg, $p<0.05$; hPBMC vs. hPBMC+αCTLA-4-treated Treg, $p>0.05$. Data represent 2 independent experiments. (FIG. 6D) Concentration of IL-2 and TNF-α in target organs of humanized mice accepting different treatments on day 6 post-transplantation. Data are shown as mean±SEM and represent 4 independent experiments (*$p<0.05$). (FIGS. 6E, 6F) Accumulation of donor $CD3^+$ T cells and $CD8^{hi}$ Treg (labeled with Dir) in target organs of humanized mice accepting different treatments on day 6 post-transplantation. Data are shown as mean±SEM and represent 4 independent experiments (*$p<0.05$; ns, no significant difference).

FIGS. 7A-7D show recipient-specific donor $CD8^{hi}$ Treg induce long-term tolerance and preserve general immunity in humanized mice. (FIG. 7A) Chimerism in humanized recipient mice ($A2^-$) before and after transplantation of allogeneic hPBMC ($A2^+$) and $CD8^{hi}$ Treg ($A2^+$). The percentage of donor ($A2^+$) and recipient ($A2^-$) original cells in human $CD45^+$ cells in peripheral blood and spleen from humanized GVHD mice at the indicated time after $CD8^{hi}$ Treg treatment are shown as mean±SEM (n=9). (FIG. 7B) Protocol for evaluation of general immunity in humanized GVHD mice after $CD8^{hi}$ Treg treatment. (FIG. 7C) The percentages of IFN-γ-producing cells in donor $CD4^+$ and $CD8^+$ T cells ($A2^+$) from peripheral blood and the levels of serum TT-specific antibodies after a booster vaccination of TT are shown (n=4 per group). (FIG. 7D) Long-term alloantigen-specific tolerance of donor-origin $CD3^+$ T cells. Donor-origin $CD3^+$ T cells ($A2^+$) were isolated from humanized mice transplanted with hPBMC and $CD8^{hi}$ Treg on day 100 post-transplantation and stimulated with irradiated recipient hPBMC (specific) or hPBMC from a third party (non-related). The proliferative responses of donor-origin T cells to specific or non-related hPBMC are shown. Data are shown as mean±SEM and represent 4 independent experiments (*$p<0.05$; ns, no significant difference).

FIGS. 8A-8D depict graft-versus-tumor (GVT) activity in humanized GVHD mice after $CD8^{hi}$ Treg treatment. (FIG. 8A) Protocol for evaluating GVT activity in humanized GVHD mice. (FIG. 8B) Survival, weight change, and tumor recurrence of humanized mice receiving PBS (n=15), donor hPBMC (n=10), donor hPBMC with donor $CD8^{hi}$ Treg (n=15) or recipient-specific $CD8^+$ T cells (n=10). hPBMC+Treg vs. hPBMC, hPBMC+recipient-specific CD8 or PBS, $p<0.001$. Data shown represent two independent experiments. (FIG. 8C) Cytotoxicity of $CD8^{hi}$ Treg and $CD4^+CD25^+$ Treg against allogeneic LCL in vitro. $CD8^{hi}$ Treg and anti-CD3/CD28-expanded $CD4^+CD25^+$ Treg (effector cells, E) from same HLA-A2+ donors were co-cultured with LCL (target cells, T) generated from HLA-A2− donors, whose hCD40-B cells were used for generating CD8$^{hi}$ Treg, at indicated E:T ratios and death of target cells are determined by PI staining. Data shown here represent means±SEM of 4 independent experiments. *p<0.05, **p<0.01. (FIG. 8D) Cytotoxicity of CD8$^{hi}$ Treg and CD4+CD25+ Treg against allogeneic LCL in vivo. 1.0×10$^5$ GFP-labelled A2− LCL were co-transplanted with 1.0×10$^6$ A2+ CD8$^{hi}$ Treg or anti-CD3/CD28-expanded CD4+CD25+ Treg into Rag2−/−γc−/− mice. Tumor recurrence of humanized mice is shown as mean±SEM and represent 4 independent experiments. LCL+CD8$^{hi}$ Treg vs. LCL+CD4+CD25+ Treg or LCL alone, p<0.05; LCL alone vs. LCL+CD4+CD25+ Treg, p>0.05.

Figure 9:
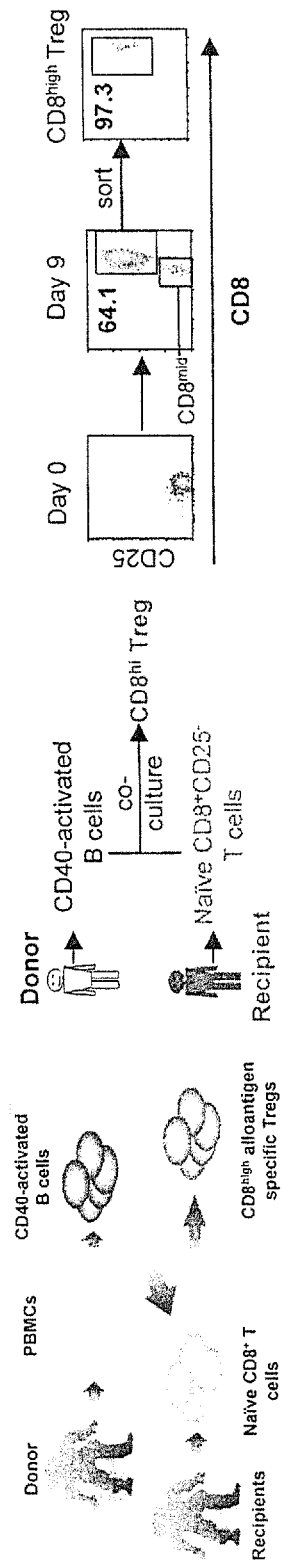
FIG. 9 shows an illustration of an example of generating of Tregs.

A general method of generating Tregs is shown in FIG. 9. Freshly purified naïve T cells (such as CD8+CD45+RA+ CD45RO−CD25− T cells) from a recipient are co-cultured with B cells (CD40-activated B cells) from a donor in suitable ratio in s suitable medium, such as RPMI 1640 medium supplemented with 10% heat-activated human AB serum. After sufficient time, such as 9 days, CD8$^{hi}$ Tregs are purified (such as by FACS sorting) and used for function assay. The Tregs can be generated without exogenous cytokines.

In one embodiment, the ratio in which the naïve T cells from a recipient are co-cultured with B cells from a donor is from to 25:1 to 2:1. In another embodiment, the ratio in which the naïve T cells from a recipient are co-cultured with B cells from a donor is from to 15:1 to 5:1. In yet another embodiment, the ratio in which the naïve T cells from a recipient are co-cultured with B cells from a donor is from to 12:1 to 8:1, such as 10:1.

In one embodiment, the naïve T cells from a recipient are co-cultured with B cells from a donor from 1 day to 25 days. In another embodiment, the naïve T cells from a recipient are co-cultured with B cells from a donor from 3 days to 20 days. In yet another embodiment, the naïve T cells from a recipient are co-cultured with B cells from a donor from 5 days to 15 days.

Materials and Methods

Animals

C57BL/10SgAiRag2−/−γc−/− (Rag2−/−γc−/−) mice were purchased from Taconic and maintained in the Laboratory Animal Unit, the University of Hong Kong. All manipulations were performed in compliance with the guidelines for the use of experimental animals by the Committee on the Use of Live Animals in Teaching and Research, Hong Kong.

Cell Isolation and Preparation hPBMC were isolated from the buffy coats of healthy donors from Hong Kong Red Cross by Ficoll-Hypaque (Pharmacia) gradient centrifugation as described before (22). The research protocol was approved by the Institutional Review Board of the University of Hong Kong/Hospital Authority Hong Kong West Cluster. Human CD8$^{hi}$ Treg were generated as described previously (23). In brief, hCD40-B cells were induced from hPBMC by NIH3T3-CD40L cells, whereas naïve CD8+CD25−CD45RA+ CD45RO− T cells were isolated from hPBMC using a naïve CD8+ T-cell isolation kit (Miltenyi Biotec). Naïve CD8+ T cells were co-cultured with allogeneic CD40-activated B cells at a T-cell:B-cell ratio of 10:1. After 9 days of incubation, CD8+ T cells expressing a high level of CD8 and CD25 were isolated by FACS sorting. The CD3+ T cell-depleted hPBMC were prepared with anti-CD3 microbeads (Miltenyi Biotec).

GVHD Model

Human allogeneic GVHD models were established in humanized mice prepared using a protocol similar to that described in our previous study (26). In brief, 4-5 week-old Rag2−/−γc−/− mice pre-treated with liposome-clodronate (VU Medisch Centrum) were sublethally irradiated (1 Gy/6 g body weight) and transplanted intraperitoneally with 3.0× 10$^7$ hPBMC (26). After 4 weeks, these humanized mice were treated as recipients and injected i.v. with 1.0×10$^7$ autologous hPBMC, 1.0×10$^7$ allogeneic hPBMC with or without 1.0×10$^6$ CD8$^{hi}$ Treg, or 1.0×10$^7$ CD3+ T cell-depleted allogeneic hPBMC one day after sublethal irradiation (1 Gy/6 g body weight). In some experiments, hPBMC and CD8$^{hi}$ Treg from HLA-A2+ donor were injected into humanized recipient mice reconstituted with HLA-A2− hPBMC. To induce GVHD by eduCD3+ T cells, humanized mice were reconstituted with hPBMC from human donor A2+ or A2−. Four weeks later, humanized mice reconstituted with hPBMC from donor A2+ were sacrificed and human eduCD3+ cells were isolated from their peripheral blood and spleen. GVHD was induced in humanized mice reconstituted with donor A2− hPBMC by 1.0×10$^6$ purified allogeneic eduCD3+ or conventional human CD3+ T cells from donor A2+. GVHD disease was scored using weight change, posture, activity, fur-texture, skin integrity and diarrhea as described by others (27).

Tumor Model

For tumor model in humanized mice, LCL cell lines were established by infecting HLA-A2− hPBMC with GFP-expressing EBV and purified by FACS sorting. Humanized mice reconstituted with HLA-A2− hPBMC were injected i.v. with 1.0×10$^5$ GFP-LCL cell lines established from the same donors 4 days before lethal irradiation. These LCL-injected mice were then transplanted with 1.0×10$^7$ allogeneic HLA-A2+ hPBMC. For tumor model in Rag2−/−γc−/− mice, 1.0× 10$^5$ GFP-labelled A2− LCL were i.v. injected alone or co-transplanted with 1.0×10$^6$ A2+ CD8$^{hi}$ Treg or CD4+ CD25+ Treg into Rag2−/−γc−/− mice. Tumor reoccurrence was assessed as the percentage of GFP-LCL in their peripheral blood.

Vaccination Protocol

Humanized mice reconstituted with HLA-A2− hPBMC were transplanted with 1.0×10$^7$ hPBMC and 1.0×10$^6$ CD8$^{hi}$ Treg from HLA-A2+ donors. At 14 days after transplantation, mice were primed with 1.5 limits of flocculation (10 of tetanus toxoid (TT) vaccine (Adventis-Pasteur) subcutaneously in the inguinal pouch region. A booster of 0.25 if of TT was given in the right hind footpad 10 days later. On day 30 post-transplantation, IFN-γ-producing cells CD4+ and CD8+ T cells in the peripheral blood of these vaccinated mice were counted by FACS analysis, and the concentration of total TT-specific IgG in the serum of humanized mice was determined by a commercial ELISA kit (Bethyl Laboratories) as we did before (26).

In Vivo Imaging hPBMC and CD8$^{hi}$ Treg were stained with Dil and Dir (Invitrogen) respectively. Dil-labeled hPBMC were injected into recipient humanized mice with Dir-labeled or unlabeled CD8$^{hi}$ Treg. The migration and accumulation of hPBMC and/or CD8$^{hi}$ Treg were visualized and analyzed with a TM 2 in vivo imaging system (CRI Maestro).

Histology

Lungs, livers, spleens, kidneys, and guts from humanized mice were harvested at indicated times. Sections were prepared according to standard protocols and stained with hematoxylin and eosin. The histopathology score was calculated based on inflammation and cell infiltration in lung, liver, kidney and gut (each organ rank 0-5) and analyzed by two independent experienced pathologists who were blinded to the treatment.

MLR Assay

The mixed lymphocyte reaction (MLR) system was established as follows: mouse spleen cells or hPBMC (recipient) were irradiated and used as stimulator cells, whereas allogeneic hPBMC (donor) were used as responder cells. Responder cells were co-cultured with stimulator cells at a 1:1 cell ratio with or without regulator ($CD8^{hi}$ Treg) for 5 days, and [$^3$H]-thymidine (PerkinElmer) was added to the culture at a concentration of 5.0 μCi/ml for the last 16 hours of incubation. Proliferation of the responder cells was analyzed by [$^3$H]-thymidine incorporation as we described before (20).

Blocking Assay

To block the effects of cytokines and granules, the following reagents and antibodies were used: anti-hIFN-γ (2 μg/ml, goat IgG), anti-hTNF-α (2 μg/ml, 28401, mouse IgG1), anti-hFas Ligand (FasL) (10 μg/ml, 100419, mouse IgG2b), Bcl-2 (Granzyme inhibitor, 2 μg/ml) (R&D Systems), anti-hCTLA-4 (10 μg/ml, ANC152.2, mouse IgG1 κ) (Ancell, Bayport), and concanamycin A (CMA) (perforin inhibitor, 10 μg/ml) (Sigma-Aldrich). For blocking, antibodies against cytokines were directly added into the culture at indicated final concentrations, whereas effector cells were incubated with Bcl-2 and CMA 1 hour before coculturing with target cells to exclude the effects of preserved ganule as we did before (39).

In Vivo Proliferation Assays

HLA-A2$^+$ allogeneic hPBMC (5×10$^6$ cells/ml) were stained with 22 μl of 0.05 mM carboxyfluorescein succinimidyl ester (CFSE) (Sigma) at 37° C. for 5 min followed by washing with PBS three times before injection into humanized recipient mice reconstituted with HLA-A2$^-$ hPBMC. On day 3, 6 and 9 post transplantation, lung and liver of recipient mice were harvested and prepared into single cell suspension. The levels of CFSE in HLA-A2$^+$ CD3$^+$ T cells were analyzed using FACS Aria-II (BD) and Flowjo software.

Cytotoxicity Assays

For determining the cytotoxicity of $CD8^{hi}$ Treg and CD4$^+$ CD25$^+$ Treg (Effector, E) against GFP-LCL (Target, T), effector cells and target cells were co-cultured at different E:T ratio in 37° C. for 4 hours with the addition of PI at the final 15 minutes. The apoptosis of target cells were analyzed using BD FACS Aria-II by back gating on GFP and PI positive cells.

Flow Cytometric Analysis

Cells were stained for surface markers with the following monoclonal antibodies: anti-hCD3-FITC (HIT3a), anti-hCD19-APC (HIB 19), anti-hCD25-APC (2A3), anti-HLA-A2-FITC (BB7.2) (BD Biosciences); anti-hCD4-Alexa-405 (S3.5), anti-hCD8-PE-Cy7 (3B5), anti-hCD45-APC (HI30) (Invitrogen); anti-hIFN-γ-FITC (4S.B3) (R&D Biosystems). All samples were acquired on BD FACSAria and analyzed by Flowjo software (Tree Star) as described previously (20).

Flowcytomix Assay

For the detection of cytokines and chemokines, the lungs, livers and guts from recipient humanized mice were harvested at the indicated times and homogenized in PBS. The concentrations of human pro-inflammatory cytokines and chemokines in these samples were detected and analyzed with human cytokine and chemokine assay kits (Bender MedSystems) as we described before (26).

Statistical Analysis

Data are shown as mean±SEM. Multiple regression analysis was used to test the differences in the body weight changes between groups adjusted for time post-transplantation. The differences in cell percentage and concentrations of pro-inflammatory cytokines/chemokines among groups were analyzed by an unpaired, two-tailed Student's t-test. The significance of differences in survival was determined by the Kaplan-Meier log-rank test. $p<0.05$ was considered to be significant.

REFERENCES AND NOTES

1. V. T. Ho, R. J. Soiffer, The history and future of T-cell depletion as graft-versus-host disease prophylaxis for allogeneic hematopoietic stem cell transplantation. *Blood* 98, 3192-3204 (2001).
2. M. Siadak, K. M. Sullivan, The management of chronic graft-versus-host disease. *Blood Rev.* 8, 154-160 (1994).
3. S. Sakaguchi, T. Yamaguchi, T. Nomura, M. Ono, Regulatory T cells and immune tolerance. *Cell* 133, 775-787 (2008).
4. E. M. Shevach, From vanilla to 28 flavors: multiple varieties of T regulatory cells. *Immunity* 25, 195-201 (2006).
5. M. Edinger, P. Hoffmann, J. Ermann, K. Drago, C. G. Fathman, S. Strober, R. S. Negrin, CD4$^+$CD25+ regulatory T cells preserve graft-versus-tumor activity while inhibiting graft-versus-host disease after bone marrow transplantation. *Nat. Med.* 9, 1144-1150 (2003).
6. K. L. Hippen, S. C. Merkel, D. K. Schirm, C. Nelson, N. C. Tennis, J. L. Riley, C. H. June, J. S. Miller, J. E. Wagner, B. R. Blazar, Generation and large-scale expansion of human inducible regulatory T cells that suppress graft-versus-host disease. *Am. J Transplant* 11, 1148-1157 (2011).
7. K. Wing, Y. Onishi, P. Prieto-Martin, T. Yamaguchi, M. Miyara, Z. Fehervari, T. Nomura, S. Sakaguchi, CTLA-4 control over Foxp3$^+$ regulatory T cell function. *Science* 322, 271-275 (2008).
8. L. Chess, H. Jiang, Resurrecting CD8+ suppressor T cells. *Nat Immunol* 5, 469-471 (2004).
9. R. Cortesini, J. LeMaoult, R. Ciubotariu, N. S. Cortesini, CD8$^+$CD28– T suppressor cells and the induction of antigen-specific, antigen-presenting cell-mediated suppression of Th reactivity. *Immunol. Rev.* 182, 201-206 (2001).
10. G. Filaci, N. Suciu-Foca, CD8+ T suppressor cells are back to the game: are they players in autoimmunity? *Autoimmun. Rev.* 1, 279-283 (2002).
11. T. R. Smith, V. Kumar, Revival of CD8+ Treg-mediated suppression. *Trends Immunol.* 29, 337-342 (2008).
12. L. Van Kaer, Comeback kids: CD8+ suppressor T cells are back in the game. *J. Clin. Invest.* 120, 3432-3434 (2010).
13. N. M. Lerret, J. L. Houlihan, T. Kheradmand, K. L. Pothoven, Z. J. Zhang, X. Luo, Donor-Specific CD8(+) Foxp3(+) T Cells Protect Skin Allografts and Facilitate Induction of Conventional CD4(+) Foxp3(+) Regulatory T Cells. *Am. J. Transplant.* 12, 2335-2347 (2012).
14. V. Ablamunits, B. Bisikirska, K. C. Herold, Acquisition of regulatory function by human CD8(+) T cells treated with anti-CD3 antibody requires TNF. *Eur. J. Immunol.* 40, 2891-2901 (2010).
15. B. Bisikirska, J. Colgan, J. Luban, J. A. Bluestone, K. C. Herold, TCR stimulation with modified anti-CD3 mAb expands CD8+ T cell population and induces CD8+ CD25+ Tregs. *J. Clin. Invest.* 115, 2904-2913 (2005).
16. P. P. Boor, H. J. Metselaar, S. D. Jonge, S. Mancham, L. J. van der Laan, J. Kwekkeboom, Human plasmacytoid dendritic cells induce CD8(+) LAG-3(+) Foxp3(+) CTLA-4(+) regulatory T cells that suppress allo-reactive memory T cells. *Eur. J. Immunol.* 41, 1663-1674 (2011).
17. M. Gilliet, Y. J. Liu, Generation of human CD8 T regulatory cells by CD40 ligand-activated plasmacytoid dendritic cells. *J. Exp. Med.* 195, 695-704 (2002).
18. S. Jiang, S. Tugulea, G. Pennesi, Z. Liu, A. Mulder, S. Lederman, P. Harris, R. Cortesini, N. Suciu-Foca, Induction of MHC-class I restricted human suppressor T cells by peptide priming in vitro. *Hum. Immunol.* 59, 690-699 (1998).
19. E. Uss, S. L. Yong, B. Hooibrink, R. A. van Lier, I. J. ten Berge, Rapamycin enhances the number of alloantigen-induced human CD103+CD8+ regulatory T cells in vitro. *Transplantation* 83, 1098-1106 (2007).
20. W. Tu, Y. L. Lau, J. Zheng, Y. Liu, P. L. Chan, H. Mao, K. Dionis, P. Schneider, D. B. Lewis, Efficient generation of human alloantigen-specific CD4+ regulatory T cells from naive precursors by CD40-activated B cells. *Blood* 112, 2554-2562 (2008).
21. J. Zheng, Y. Liu, Y. L. Lau, W. Tu, CD40-activated B cells are more potent than immature dendritic cells to induce and expand CD4(+) regulatory T cells. *Cell. Mol. Immunol.* 7, 44-50 (2010).
22. J. Zheng, Y. Liu, G. Qin, K. T. Lam, J. Guan, Z. Xiang, D. B. Lewis, Y. L. Lau, W. Tu, Generation of human Th1-like regulatory CD4+ T cells by an intrinsic IFN-gamma- and T-bet-dependent pathway. *Eur. J. Immunol.* 41, 128-139 (2011).
23. J. Zheng, Y. Liu, G. Qin, P. L. Chan, H. Mao, K. T. Lam, D. B. Lewis, Y. L. Lau, W. Tu, Efficient induction and expansion of human alloantigen-specific CD8 regulatory T cells from naive precursors by CD40-activated B cells. *J. Immunol.* 183, 3742-3750 (2009).
24. F. Issa, J. Hester, R. Goto, S. N. Nadig, T. E. Goodacre, K. Wood, Ex Vivo-Expanded Human Regulatory T Cells Prevent the Rejection of Skin Allografts in a Humanized Mouse Model. *Transplantation* 90, 1321-1327 (2010).
25. S. N. Nadig, J. Wieckiewicz, D. C. Wu, G. Warnecke, W. Zhang, S. Luo, A. Schiopu, D. P. Taggart, K. J. Wood, In vivo prevention of transplant arteriosclerosis by ex vivo-expanded human regulatory T cells. *Nat. Medicine.* 16, 809-813 (2010).
26. W. Tu, J. Zheng, Y. Liu, S. F. Sia, M. Liu, G. Qin, I. H. Ng, Z. Xiang, K. T. Lam, J. S. Peiris, Y. L. Lau, The aminobisphosphonate pamidronate controls influenza pathogenesis by expanding a gammadelta T cell population in humanized mice. *J. Exp. Med.* 208, 1511-1522 (2011).
27. K. R. Cooke, L. Kobzik, T. R. Martin, J. Brewer, J. Delmonte, Jr., J. M. Crawford, J. L. Ferrara, An experimental model of idiopathic pneumonia syndrome after bone marrow transplantation: I. The roles of minor H antigens and endotoxin. *Blood* 88, 3230-3239 (1996).
28. W. Krenger, G. R. Hill, J. L. Ferrara, Cytokine cascades in acute graft-versus-host disease. *Transplantation* 64, 553-558 (1997).
29. J. L. Ferrara, R. Levy, N. J. Chao, Pathophysiologic mechanisms of acute graft-vs.-host disease. *Biol. blood marrow Transplant.* 5, 347-356 (1999).
30. A. J. Beres, D. Haribhai, A. C. Chadwick, P. J. Gonyo, C. B. Williams, W. R. Drobyski, CD8+ Foxp3+ regulatory T cells are induced during graft-versus-host disease and mitigate disease severity. *J. Immunol.* 189, 464-474 (2012).
31. R. J. Robb, K. E. Lineburg, R. D. Kuns, Y. A. Wilson, N. C. Raffelt, S. D. Olver, A. Varelias, K. A. Alexander, B. E. Teal, T. Sparwasser, G. J. Hammerling, K. A. Markey, M. Koyama, A. D. Clouston, C. R. Engwerda, G. R. Hill, K. P. MacDonald, Identification and expansion of highly suppressive CD8(+)FoxP3(+) regulatory T cells after experimental allogeneic bone marrow transplantation. *Blood* 119, 5898-5908 (2012).
32. X. L. Li, S. Menoret, S. Bezie, L. Caron, D. Chabannes, M. Hill, F. Halary, M. Angin, M. Heslan, C. Usal, L. Liang, C. Guillonneau, B. Le Mauff, M. C. Cuturi, R. Josien, I. Anegon. Mechanism and Localization of CD8 Regulatory T Cells in a Heart Transplant Model of Tolerance. *J. Immunol.* 185, 823-833 (2010).
33. D. H. Fowler, R. E. Gress, Th2 and Tc2 cells in the regulation of GVHD, GVL, and graft rejection: considerations for the allogeneic transplantation therapy of leukemia and lymphoma. *Leuk. Lymphoma* 38, 221-234 (2000).
34. S. Sakaguchi, K. Wing, Y. Onishi, P. Prieto-Martin, T. Yamaguchi, Regulatory T cells: how do they suppress immune responses? *Int. immunol.* 21, 1105-1111 (2009).
35. K. Wing, T. Yamaguchi, S. Sakaguchi: Cell-autonomous and -non-autonomous roles of CTLA-4 in immune regulation. *Trends in immunol.* 32, 428-433 (2011).
36. T. R. Malek, I. Castro, Interleukin-2 receptor signaling: at the interface between tolerance and immunity. *Immunity* 33, 153-165 (2010).
37. D. K. Tennakoon, R. S. Mehta, S. B. Ortega, V. Bhoj, M. K. Racke, N. J. Karandikar, Therapeutic induction of regulatory, cytotoxic CD8+ T cells in multiple sclerosis. *J. Immunol.* 176, 7119-7129 (2006).
38. K. Trandem, J. Zhao, E. Fleming, S. Perlman, Highly Activated Cytotoxic CD8 T Cells Express Protective IL-10 at the Peak of Coronavirus-Induced Encephalitis. *J. Immunol.* 186, 3642-3652 (2011).
39. G. Qin, H. Mao, J. Zheng, S. F. Sia, Y. Liu, P. L. Chan, K. T. Lam, J. S. Peiris, Y. L. Lau, W. Tu, Phosphoantigen-expanded human gammadelta T cells display potent cytotoxicity against monocyte-derived macrophages infected with human and avian influenza viruses. *J. Infect. Dis.* 200, 858-865 (2009).

What is claimed is:

1. A method for inhibiting a patient-recipient from rejecting a tissue graft or an organ transplant from a donor due to an allogeneic rejection, comprising:
   obtaining a sample of naïve $CD8^+CD25^-$ T cells from the patient-recipient;
   co-culturing activated B cells from the donor of the tissue graft or organ transplant with naïve $CD8^+CD25^-$ T cells from the patient-recipient in a ratio of 1:2 to 1:25 for a period of time sufficient to generate alloantigen-specific human $CD8^{hi}$ regulatory T cells, wherein co-culturing is performed in the absence of exogenous cytokines; and
   administering the alloantigen-specific human $CD8^{hi}$ regulatory T cells to the patient-recipient of the tissue graft or organ transplant.

2. The method according to claim 1, wherein the alloantigen-specific human $CD8^{hi}$ regulatory T cells comprise $CD8^{hi}CD25^+Foxp3^+$ regulatory T cells and the activated B cells comprise allogeneic CD40-activated B cells.

3. The method according to claim 1, wherein the period of time is from 1 day to 25 days.

\* \* \* \* \*